United States Patent
Schneider et al.

(10) Patent No.: US 7,566,452 B1
(45) Date of Patent: Jul. 28, 2009

(54) CANCER TREATMENT WITH ENDOTHELIN RECEPTOR ANTAGONISTS

(75) Inventors: Robert J. Schneider, New York, NY (US); Sumayah Jamal, New York, NY (US)

(73) Assignee: New York University, New York, NY (US)

( * ) Notice: Subject to any disclaimer, the term of this patent is extended or adjusted under 35 U.S.C. 154(b) by 0 days.

(21) Appl. No.: 09/305,084

(22) Filed: May 4, 1999

(51) Int. Cl.
*A61K 39/395* (2006.01)
*A61K 38/00* (2006.01)
*G01N 33/53* (2006.01)

(52) U.S. Cl. .................................. 424/156.1; 514/2

(58) Field of Classification Search ............... 435/4, 435/6, 7.1, 7.21, 7.23; 514/1, 2; 424/130.1
See application file for complete search history.

(56) References Cited

U.S. PATENT DOCUMENTS

| | | | |
|---|---|---|---|
| 4,190,496 A | 2/1980 | Rubenstein et al. | |
| 4,376,110 A | 3/1983 | David et al. | |
| 4,946,778 A | 8/1990 | Ladner et al. | |
| 4,980,286 A | 12/1990 | Morgan et al. | |
| 5,082,838 A | 1/1992 | Naka et al. | |
| 5,114,918 A | 5/1992 | Ishikawa et al. | |
| 5,187,195 A | 2/1993 | Oohata et al. | |
| 5,198,548 A | 3/1993 | Beylin et al. | |
| 5,208,243 A | 5/1993 | Peglion et al. | |
| 5,240,910 A | 8/1993 | Lam et al. | |
| 5,248,807 A | 9/1993 | Fujimoto et al. | |
| 5,270,313 A | 12/1993 | Burri et al. | |
| 5,334,598 A | 8/1994 | Bagley et al. | |
| 5,352,659 A | 10/1994 | Wakimasu et al. | |
| 5,352,800 A | 10/1994 | Bills et al. | |
| 5,382,569 A | 1/1995 | Cody et al. | |
| 5,464,853 A | 11/1995 | Chan et al. | |
| 5,550,110 A | 8/1996 | Cody et al. | |
| 5,573,762 A * | 11/1996 | Ferrara et al. ............. | 424/145.1 |
| 5,585,089 A | 12/1996 | Queen et al. | |
| 6,063,911 A * | 5/2000 | Vournakis et al. | |

FOREIGN PATENT DOCUMENTS

| | | |
|---|---|---|
| CA | 2067288 | 10/1992 |
| CA | 2071193 | 12/1992 |
| EP | A1 0 436 189 | 7/1991 |
| EP | A1 0 496 452 | 7/1992 |
| EP | A1 0 558 258 | 9/1993 |
| EP | A1 0 569 193 | 11/1993 |
| EP | 1 181 555 B1 | 12/2008 |
| WO | WO 92/06180 | 4/1992 |
| WO | WO 92/20316 | 11/1992 |
| WO | WO 92/22635 | 12/1992 |
| WO | WO 93/14188 | 7/1993 |
| WO | WO 93/20221 | 10/1993 |
| WO | WO 94/27979 | 12/1994 |

OTHER PUBLICATIONS

Johnson and Goldin. The clinical impact of screening and other experimental tumor studies. Cancer Treatment Reviews 2:1-31, 1975.*
Lahav et al. An endothelin receptor B antagonist inhibits growth and induces cell death in human melanoma cells in vitro and in vivo. Proc. Natl. Acad. Sci. USA 96:11496-11500, Sep. 1999.*
Kikuchi et al, Biochemical and Biophysical Research Communications, 1996, vol. 219, pp. 734-739.*
Nelson et al, Cancer Research, 1996, vol. 56, pp. 663-668.*
F. Meins, 'Cancer as a Problem in Development', In: Cancer: The Outlaw Cell, 1988, pp. 97-98.*
Verma et al (Nature, 1997, vol. 389, pp. 239-242).*
Eck et al (Gene-Based Therapy, In: The Pharmacological Basis of Therapeutics, Goodman and Gilman, Ed.s, 1996, pp. 77-101).*
Orkin et al state ( "Report and Recommendation of the Panel to Assess the NIH Investment in Research on Gene Therapy", NIH, 1995).*
The abstract of Ramel et al, Environmental Science Research, 1984, vol. 41, pp. 97-112.*
James and Gibson (Blood, 1998, vol. 91, pp. 371-382).*
Bagnato et al (Cells Tissues Organs, 2007, vol. 185, pp. 85-94).*
Adner et al., 1994, "Human endothelin $ET_A$ receptor antisense oligodeoxynucleotides inhibit endothelin-1 evoked vasoconstriction", *Eur. J. Pharm.* 261:281-284.
Barber et al., 1996, "Chronic increases in blood flow upregulate endothelin-B receptors in arterial smooth muscle", *Am. J. Physiol.* 270:H65-H71.
Battistini and Dussault, 1998, "Blocking of the endothelin system: the development of receptor antagonists", *Pul. Pharm. Therap.* 11:97-112.
Chan et al., 1998, "The discovery and structure-activity relationships of nonpeptide, low molecular weight antagonists selective for the endothelin $ET_B$ receptor", *Bioorganic & Medicinal Chemistry* 6:2301-2316.
Davenport and Battistini, 2002, "Classification of endothelin receptors and antagonists in clinical development", *Clinical Science* 103:1S-3S.
D'Orléans-Juste et al., 1997, "DNA antisense strategies in the study of receptors for vasoactive peptides, and of growth and wound-healing factors", *Molec. Cell. Biochemistry* 172:199-211.

(Continued)

Primary Examiner—Karen A Canella
(74) Attorney, Agent, or Firm—Jones Day

(57) ABSTRACT

The present invention relates to therapeutic protocols and pharmaceutical compositions designed to treat and prevent cancer. More specifically, the present invention relates to a novel method of treating cancer using antagonists to the endothelin B receptor (ETB) or inactive mimic forms of endothelin-1. The pharmaceutical compositions of the invention are capable of selectively inhibiting the early events associated with the development of cancer. The present invention further relates to screening assays to identify compounds which inhibit ETB activation.

16 Claims, 6 Drawing Sheets

OTHER PUBLICATIONS

Figure 2A:
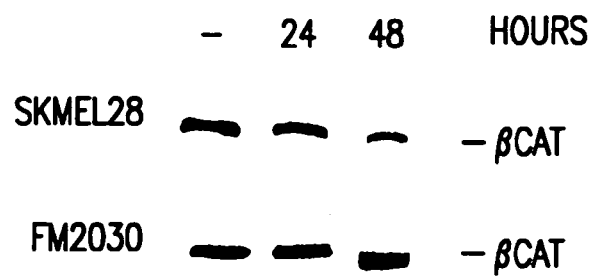

Douglas, 1997, "Clinical development of endothelin receptor antagonists", *TiPS* 18:408-412.
Mederski et al., 1999, "Benzofuro [3,2-b] Pyridines as mixed $ET_A/ET_B$ and selective $ET_B$ endothelin receptor antagonists", *Bioorg. Med. Chem. Lett.* 9:619-622.
Ninomiya et al., 1998, "Paracrine endothelin signaling in the control of basal cell proliferation in guinea pig tracheal epithelium", *J. Pharmacol. Exp. Therap.* 286:469-480.
Kikuchi et al., 1996, Biochem. Biophys. Res. Commun., 219:734-739.
Albino et al., 1991, Cancer Res., 51:4815-4820.
Arai et al., 1990, Nature, 348:730-732.
Becker et al., 1992, Oncogene, 7:2303-2313.
Benigni et al., 1993, Kidney Int., 44:440-444.
Bird, 1988, Science, 242:423-426.
Bolger et al., 1991, Can. J. Physiol. Pharmacol., 69: 406-413.
Brabant, et al., 1993, Cancer Research, 53: 4987-4993.
Brooks et al., 1991, Eur. J. Pharm. 194:115-117.
Calabresi P. and Chabner B. A., Goodman and Gilman The Pharmacological Basis of Therapeutics, Pergamon Press, 8th Edition, pp. 1202-1204.
Calabresi P. and Chabner B. A., Goodman and Gilman The Pharmacological Basis of Therapeutics, Pergamon Press, 8th Edition, pp. 1209-1216.
Clozel et al., 1993, Nature 365:759-761.
Cody et al., 1993, Med. Chem. Res. 3:154-162.
Daniel et al., 1997, *BioEssays*, 19(10): 883-891.
Doherty, 1992, J. Med. Chem., 35:1493-1508.
Dorudi, et al., 1993, American Journal of Pathology, 142:981-986.
Dotto et al., 1989, J. Cell Biol., 109:3115-3128.
Fujimoto et al., 1992, FEBS Lett., 305:41-44.
Furchgott and Zawadski, 1980, Nature, 288:373-376.
Gamallo, et al., 1993, American Journal of Pathology, 142:987-993.
Greenspan & Bona, 1993, FASEB J., 7(5):437-444.
Halaban et al., 1992, Oncogene, 7:2195-2206.
Halaban, 1991, Cancer Metastasis Rev., 10:129-140.
Herren, et al., 1998, *Mol. Biol. Cell.*, 9:1589-601.
Hsu, et al., 1996, *J. Investig. Dermatol. Symp. Proc.*, 1:188-94.
Hunt et al., 1991, *Biorganic and Medic. Chem. Lett.*, 1:33-38.
Imokawa, et al., 1992, *J. Biol. Chem.*, 267:24675-80.
Imokawa, et al., 1996, *Biochem. J.*, 314:305-12.
Ishikawa et al., 1992, J.M d. Chem., 35:2139-2142.
Kanno et al., 1990, J. Amer. Med. Assoc. , 264:2868.
Karaki et al., 1994, *Biochem. Biophys. Res. Commun.*, 205:168-173.
Köck et al., 1991, Cancer Treat. Res., 54:41-66.
Kohzuma et al., 1994, *Neuroreport*, 5:2653-2656.
Koller & Smithies, 1989, Proc. Natl. Acad. Sci. USA, 86:8932-8935.
Krutmann et al., 1992, J. Invest. Dermatol., 98:923-928.
Lam, K.S. et al., 1991, Nature, 354:82-84.
Lu et al., 1992, Proc. Natl. Acad. Sci., 89:9215-9219.
Marsault, et al., 1991, *Biochem. Biophys. Res. Commun.*, 179:1408-13.
Miyata et al., 1992, J. Antibiot., 45:74-8.
Miyata et al., 1992, J. Antibiot., 45:1041-1046.
Miyata et al., 1992 J. Antibiot, 45:1029-1040.
Moll, et al., 1993, American Journal of Pathology, 143: 1731-1742.
Morel et al., 1989, Eur. J. Pharmacol., 167: 427-428.
Nakajima et al., 1991, J. Antibiot., 44:1348-1356.
Nishikibe et al., 1993, Life Sci., 52:717-724.
Nishiyama et al., 1995, *Jpn.J. Pharmacol.* Japan, 69(4):391-398.
Nissonoff, 1991, J. Immunol., 147(8):2429-2438.
Oka, et al., 1993, Cancer Research, 53: 1696-1701.
Okazawa, et al., 1998, *J. Biol. Chem.*, 273:12584-92.
Oshashi et al., 1992, J. Antibiot, 45:1684-1685.
Otto, et al., 1994, Cancer Research, 54: 3120-3123.
Palmer et al., 1987, Nature, 327:524-526.
Pignatelli, et al., Journal of Pathology, 1994, 174:243-248.
Pizarro, et al. 1994, Br. J. Cancer, 69(1):157-162.
Rodeck et al., 1991, J. Invest. Dermatol., 97:20-26.
Rodeck and Herlyn, 1991, Cancer Metastasis Rev., 10:89-101.
Rosenfeld et al., 1992, Cell, 68:143-155.
Saida et al., 1989, J. Biol. Chem., 264:14613-14616.
Saito et al. (1990) Hypertension, 15:734-738.
Sakurai et al. (1990) Nature, 348:732-735.
Saunders Company, Philadelphia, pp. 340-341 Cellular and Molecular Immunology, 1991 eds., Abbas A. K., Lichtman, A. H., Pober, J. S..
Scaffidi et al., 1999, *J. Biol. Chem.*, 3:1541-1548.
Schipper, et al., 1991, Cancer Research, 51:6328-6337.
Shibata et al., 1996, *Peptide Chemistry 1995, Proc. of the 33rd Symp. on Peptide Chem.*, Sapporo, Japan, pp. 281-284.
Shih et al., 1994, *Am. J. Pathol.*, 145:837-45.
Shimoyama et al., 1992, Cancer Res., 52:5770-5774.
Songyang, Z. et al., 1993, Cell, 72:767-778.
Tanaka et al., 1994, *Mol. Pharmacol.*, 45:724-730.
Tang, et al., 1994, *J. Cell. Sci.*, 107:983-92.
Thornberry, et al., 1998, *Science*, 261:1312-8.
Tohma, et al., 1992, Cancer Research, 52: 1981-1987.
Tomita et al., 1989, N. Engl. J. Med. 321:1127.
Umbas, et al., Cancer Research, 1992, 52:5104-5109.
Urade et al.,1992, *FEBS Lett.*, 311:12-16.
Valyi-Nagy et al., 1993, *Lab Invest.*, 69:152-9.
Vanhoutte et al., 1986, Annual Rev. Physiol., 48: 307-320.
Vermeulen, et al., 1996, *Pathol. Res. Pract.*, 192: 694-707.
von Geldem et al., 1991, Peptide Res., 4: 32-35.
Wu and Wu, 1987, J. Biol. Chem., 262:4429-4432.
Yamanishi et al., 1992, Cancer Res., 52:5024-5029.
Zijlstra et al., 1989, Nature, 342:435-438.
Jiang et al., 1995, "Regulation of the expression of E-cadherin on human cancer cells by gamma-linolenic acid (GLA)," Cancer Res. 55(21):5043-8.

* cited by examiner

```
              -  24  48   HOURS
SKMEL28  ━  ━   ─   -ECAD
FM2030   ━  ─   ─   -ECAD
```
FIG. 1A
| CELL LINE | ↓ ECAD |
|---|---|
| CL-NHEM | + |
| M20 | + |
| WM-266-4 | + |
| WM-115 | n/a |
| A375 | n/a |
FIG. 1B
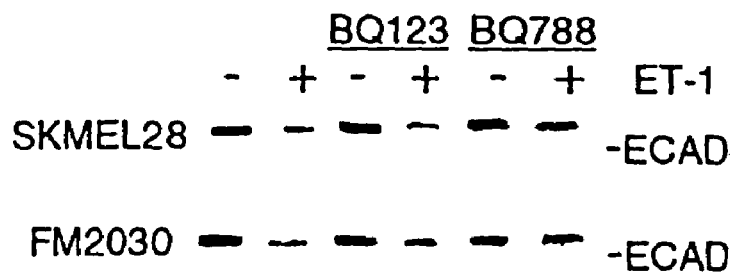
FIG. 1C
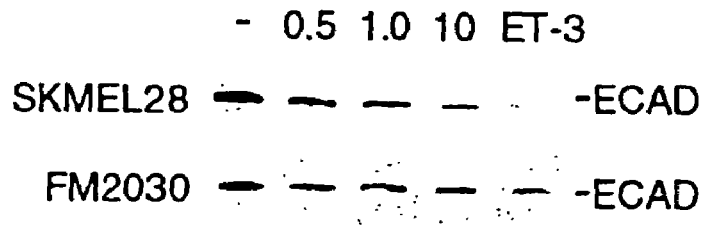
FIG. 1D

Figure 3D:
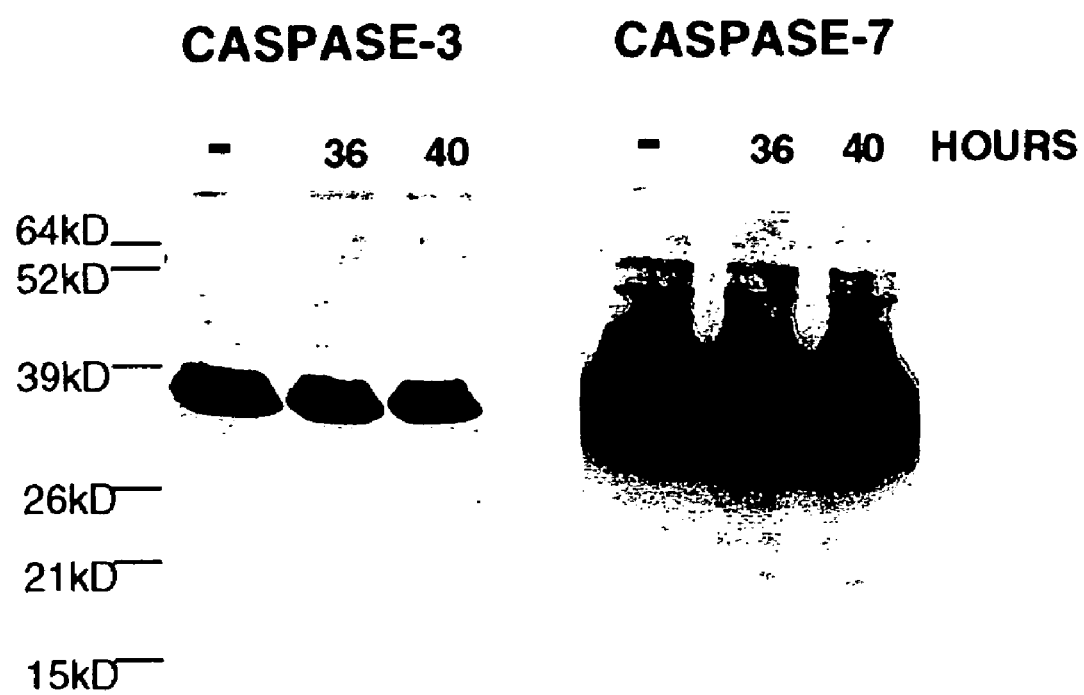

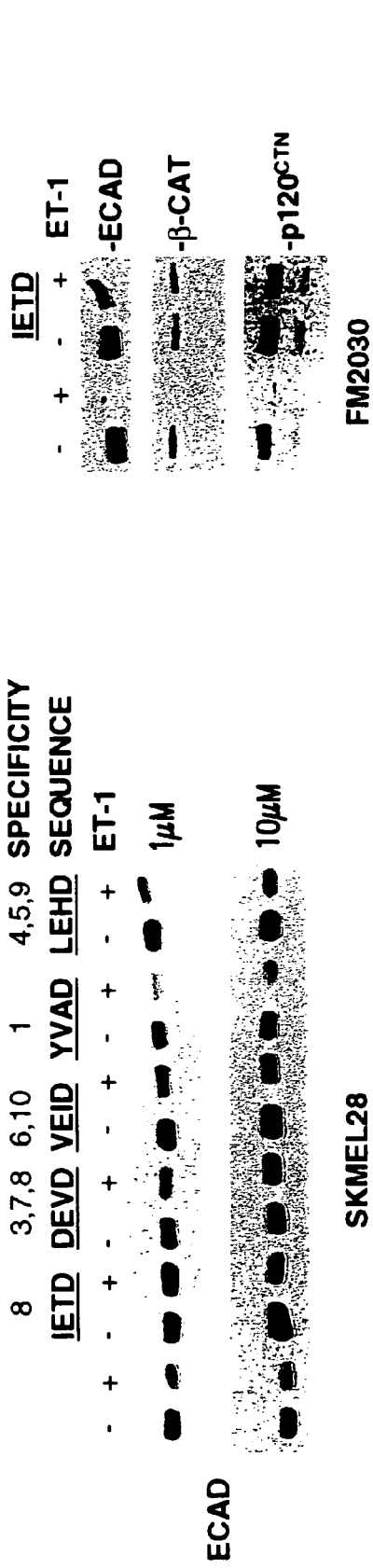
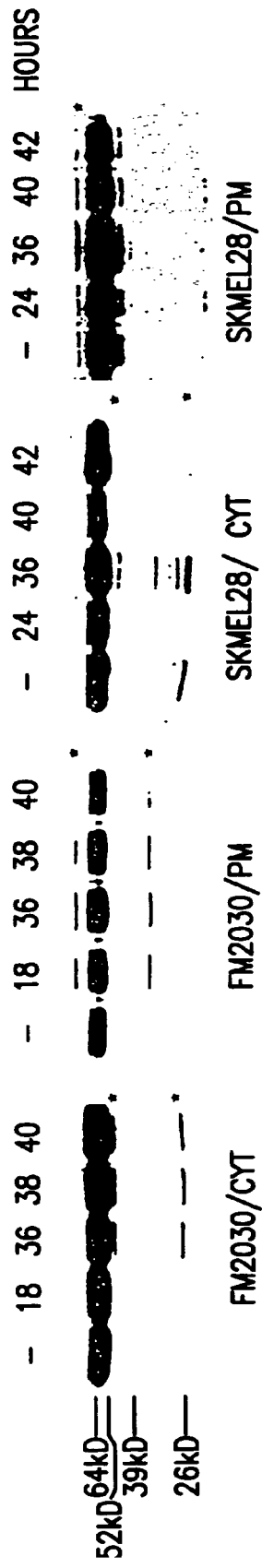
FIG.3A
FIG.3B
FIG.3C

No ET-1      ET-1

SKMEL28

FM2030

SKMEL28

No ET-1      ET-1
FM2030
FIG.4G      FIG.4H
FM2030
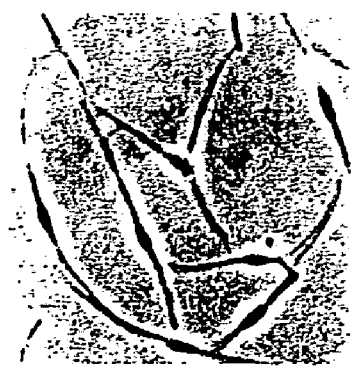
FIG.4I      FIG.4J

CANCER TREATMENT WITH ENDOTHELIN RECEPTOR ANTAGONISTS

1 INTRODUCTION

The present invention relates generally to the field of cancer prevention and treatment. More particularly, the present invention relates to compositions, and methods of using the compositions for the prevention and/or treatment of melanoma. The compositions of the invention are capable of selectively inhibiting the early events that are associated with melanoma development. In addition, the compositions of the invention are useful for the treatment of existing melanoma.

The present invention also relates to pharmaceutical formulations containing the compositions of the invention, methods of administering the pharmaceutical formulations and to screening assays to identify additional compounds which are capable of preventing and/or treating cancer.

2 BACKGROUND OF THE INVENTION

2.1 Cancer

In the United States, cancer accounts for over 500,000 deaths annually, a toll second only to that from cardiovascular diseases. Current statistics suggest that approximately 30 percent of Americans will develop cancer within their lifetime, of whom about two-thirds will die as a result of their disease.

Cancer is not fully understood on the molecular level. It is known that exposure of a cell to a carcinogen, such as certain viruses, certain chemicals or radiation, leads to DNA alteration that inactivates a "suppressive" gene or activates an "oncogene". Suppressive genes are growth regulatory genes which, upon mutation, can no longer control cell growth. Oncogenes are initially normal genes (called protoncogenes) that by mutation or altered context of expression become transforming genes. The products of transforming genes cause inappropriate cell growth. More than twenty different normal cellular genes can become oncogenes by genetic alteration. Transformed cells differ from normal cells in many ways, including cell morphology, cell-to-cell interactions, membrane content, cytoskeletal structure, protein secretion, gene expression and mortality (transformed cells can grow indefinitely).

All of the various cell types of the body can be transformed into benign or malignant tumor cells. The most frequent tumor site is lung, followed by colorectal, breast, prostate, bladder, pancreas and then ovary. Other prevalent types of cancer include leukemia, central nervous system cancers, including brain cancer, melanoma, lymphoma, erythroleukemia, uterine cancer and head and neck cancer.

Cancer is now primarily treated with one, or a combination, of three types of therapies: surgery, radiation and chemotherapy. However, results with these therapies, while beneficial in some cancers, have had only marginal or no effect in many others. Furthermore, these therapies often are associated with unacceptable toxicity.

Both radiation and surgery suffer from the same theoretical drawback. It has been recognized that, given that a single malignant cell can give rise to sufficient progeny to kill the host, the entire population of neoplastic cells must be eradicated. See generally, Goodman and Gilman The Pharmacological Basis of Therapeutics (Pergamon Press, 8th Edition) (pp. 1202-1204). This concept of "total cell kill" implies that total excision of a tumor is necessary for a surgical approach, and complete destruction of all cancer cells is needed in a radiation approach, if one is to achieve a cure. In practice, this is rarely possible; indeed, where there are metastases, it is impossible.

The term "chemotherapy" simply means the treatment of disease with chemical substances. The father of chemotherapy, Paul Ehrlich, imagined the perfect chemotherapeutic as a "magic bullet;" such that the chemotherapeutic would kill invading organisms without harming the host. This target specificity is sought in all types of chemotherapeutics, including anticancer agents.

Target specificity, however, has been the major problem with anticancer agents. In the case of anticancer agents, the drug needs to distinguish between host cells that are cancerous and host cells that are not cancerous. The vast bulk of anticancer drugs are indiscriminate at this level. Typically, anticancer agents have negative hematological effects (e.g., cessation of mitosis and disintegration of formed elements in marrow and lymphoid tissues), and immunosuppressive action (e.g., depressed cell counts), as well as a severe impact on epithelial tissues (e.g., intestinal mucosa), reproductive tissues (e.g., impairment of spermatogenesis) and the nervous system. See, P. Calabresi and B. A. Chabner, In: Goodman and Gilman The Pharmacological Basis of Therapeutics (Pergamon Press, 8th Edition) (pp. 1209-1216).

Although a number of chemotherapeutic agents have been identified and are currently used for the treatment of cancer, new agents are sought that are efficacious and which exhibit low toxicity toward healthy cells.

2.2 Melanoma

Melanomas are malignant neoplasms which are aggressive, frequently metastatic tumors derived from either melanocytes or melanocyte related nevus cells ("Cellular and Molecular Immunology" (1991) (eds) Abbas A. K., Lichtman, A. H., Pober, J. S.; W. B. Saunders Company, Philadelphia: pages 340-341). Melanomas arise most commonly in the skin of any part of the body, or in the eye, and, rarely, in the mucous membranes of the genitalia, anus, oral cavity or other sites.

Melanocytes, which are the pigment producing cells of the epidermis, undergo malignant transformation in malignant melanoma. Through their numerous dendritic processes, melanocytes contact multiple keratinocytes, the predominant cell type of the epidermis. The adhesion molecule E-cadherin mediates the contact between the keratinocytes and the melanocytes. I. T. Valyi-Nagy, et al., *Lab Invest.*, 69:152-9 (1993); A. Tang, et al., *J. Cell. Sci.*, 107:983-92 (1994).

In normal skin, melanocytes are restricted to the basal layer of the epidermis, however, in malignant melanoma, melanoma cells grow throughout all layers of the epidermis, as well as in the underlying dermis. The acquisition of invasiveness is almost always accompanied by the down-regulation of E-cadherin, which is a tumor invasion suppressor. S. Vermeulen, et al., *Pathol. Res. Pract.*, 192: 694-707 (1996). Moreover, loss of contact with keratinocytes causes melanocytes to dedifferentiate and to express melanoma-associated cell-surface antigens. I. M. Shih, et al. *Am. J. Pathol.*, 145: 837-45 (1994).

Melanomas, which make up approximately three percent of all skin cancers, are the leading cause of death from any skin disease. Further, the worldwide increase in melanoma is unsurpassed by any other neoplasm with the exception of lung cancer in women ("Cellular and Molecular Immunology" (1991) (eds) Abbas, A. K., Lechtiman, A. H., Pober, J. S.; W. B. Saunders Company Philadelphia pages: 340-342; Kirkwood and Agarwala (1993) Principles and Practice of Oncology 7:1-16). Even when melanoma is apparently localized to the skin, up to 30% of the patients will develop systemic metastasis and the majority will die (Kirkwood and Agarwala (1993) Principles and Practice of Oncology 7:1-16).

Over the past four decades, the incidence of melanoma has been increasing at a higher rate than any other type of cancer. In the Connecticut Registry, between 1935 and 1939, the incidence of melanoma was $1.2/10^5$ persons/year; this increased to $4.8/10^5$ persons/year in 1965-1969, to $7.2/10^5$ persons/year in 1976-1977 and to $9/10^5$ persons/year in 1979-1980. By the year 2000, one in 90 Caucasians in the United States is expected to develop the disease (Rigel et al., 1987, J. Am. Acad. Dermatol. 17:1050-1053). In addition, due to the depletion of the Earth's ozone layer, the Environmental Protection Agency has estimated an annual increase of 2 million cases of melanoma by the year 2050. While an increasing proportion of melanomas are diagnosed sufficiently early to respond to surgical treatment and achieve a greater than 90% ten-year survival rate, it is estimated that greater than 7,000 individuals suffering from metastatic melanoma will die in the United States each year.

Melanomas are highly variable with respect to aberrant gene expression and chromosomal lesions but share a common characteristic of an acquired independence from environmental growth factors that are needed for proliferation of normal melanocytes (Halaban, 1991, Cancer Metastasis Rev. 10:129-140). In normal melanocyte proliferation as well as uncontrolled melanoma growth, receptors with tyrosine kinase activity, such as certain growth factor receptors, appear to play an important role (Id.; Becker et al., 1992, Oncogene 7:2303-2313). Various studies have suggested that a number of growth factors may be involved in melanomagenesis (Kock et al., 1991, Cancer Treat. Res. 54:41-66; Rodeck and Herlyn, 1991, Cancer Metastasis Rev. 10:89-101; Rodeck et al., 1991, J. Invest. Dermatol. 97:20-26); such growth factors include basic fibroblast growth factor (Albino et al., 1991, Cancer Res. 51:4815-4820; Rodeck and Herlyn, 1991, Cancer Metastasis Rev. 10:89-101; Dotto et al., 1989, J. Cell Biol. 109:3115-3128; contradicted by Yamanishi et al., 1992, Cancer Res. 52:5024-5029); transforming growth factors alpha and beta (Albino et al., 1991, Cancer Res. 51:4815-4820; Rodeck and Herlyn, 1991, Cancer Metastasis Rev. 10:89-101); hepatocyte growth factor/scatter factor (Halaban et al., 1992, Oncogene 7:2195-2206); tumor necrosis factor alpha and/or beta (Kimbauer et al., 1992, J. Invest. Dermatol. 98:320-326; Krutmann et al., 1992, J. Invest. Dermatol. 98:923-928); platelet derived growth factor (Rodeck and Herlyn, 1991, Cancer Metastasis Rev. 10:89-101); and various interleukins (Kimbauer et al., 1992, J. Invest. Dermatol. 98:320-326; partly contradicted by Lu et al., 1992, Proc. Natl. Acad. Sci. 89:9215-9219).

For patients with metastatic melanoma not amenable to surgical extirpation, treatment options are limited. 5-(3,3-Dimethyl-1-triazenyl)-1-H-imidaz-ole-4-carboxamide (dacarbazine, DTIC) is the most efficacious single chemotherapeutic agent for melanoma, having an overall response rate of 24%. But the duration of response to DTIC is generally quite poor. Combination therapy with other synthetic and recombinant agents, including N,N'-bis(2-chloroethyl)-N-nitrosurea (carmustine, BCNU), cisplatin, tamoxifen, interferon-alpha (INF-α) and interleukin-2 (IL-2), has a higher response rate (e.g., 30-50%) in some trials, but a durable complete response rate is uncommon and toxicity is increased. Sequential chemotherapy has promise, but, clearly, current treatment options for individuals suffering from metastatic melanoma are unsatisfactory.

Various drugs derived from natural products, such as adriamycin (doxorubicin) derivatives, bleomyciin, etoposide and vincristine, and their derivatives, have been tested for efficacy against melanoma either as single agents or in combination therapy. However, similar to the synthetic and recombinant compounds, these compounds exhibit low response rates, transient complete responses and high toxicities.

Thus, the literature is diverse and occasionally contradictory regarding the genesis and progression of melanoma, as well as for the treatment of melanomas. Furthermore, it is unclear what factors are involved in the initiation of events which lead to melanoma, as opposed to those operative in the progression of disease.

2.2.1 Endothelins

The vascular endothelium releases a variety of vasoactive substances, including the endothelium-derived vasoconstrictor peptide, endothelin (ET) (see, E., Vanhoutte et al. (1986) Annual Rev. Physiol. 48: 307-320; Furchgott and Zawadski (1980) Nature 288: 373-376). ET, which was originally identified in the culture supernatant of porcine aortic endothelial cells (see, Yanagisawa et al. (1988) Nature 332: 411-415), is a potent twenty-one amino acid peptide vasoconstrictor. It is one of the most potent vasopressors known and is produced by numerous cell types, including the cells of the endothelium, trachea, kidney and brain. ET is synthesized as a two hundred and three amino acid precursor, preproendothelin, that contains a signal sequence which is cleaved by an endogenous protease to produce a thirty-eight (human) or thirty-nine (porcine) amino acid peptide. This intermediate, referred to as big ET, is processed in vivo to the mature biologically active form by a putative ET-converting enzyme (ECE) that appears to be a metal-dependent neutral protease (see, e.g., Kashiwabara et al. (1989) FEBS Lttrs. 247: 73-76). Cleavage of big ET is required for induction of physiological responses (see, e.g., von Geldern et al. (1991) Peptide Res. 4: 32-35). In porcine aortic endothelial cells, the thirty-nine amino acid big ET intermediate is hydrolyzed at the $Trp.^{21}$-$Val.^{22}$ bond to generate ET-1 and a C-terminal fragment. A similar cleavage occurs in human cells from a thirty-eight amino acid intermediate. Three distinct ET isopeptides, ET-1, ET-2 and ET-3, that exhibit potent vasoconstrictor activity, have been identified.

The family of the three isopeptides, ET-1, ET-2 and ET-3 are encoded by a family of three genes (see, Inoue et al. (1989) Proc. Natl. Acad. Sci. USA 86: 2863-2867; see, also Saida et al. (1989)J. Biol. Chem. 264: 14613-14616). The nucleotide sequences of the three human genes are highly conserved within the region encoding the mature 21 amino acid peptides and the C-terminal portions of the peptides are identical.

Release of ET from cultured endothelial cells is modulated by a variety of chemical and physical stimuli and appears to be regulated at the level of transcription and/or translation. Expression of the gene encoding ET-1 is increased by chemical stimuli, including adrenaline, thrombin and $Ca^{2+}$ ionophore. The production and release of ET from the endothelium is stimulated by angiotensin II, vasopressin, endotoxin, cyclosporine and other factors (see, Brooks et al. (1991) Eur. J. Pharm. 194:115-117), and is inhibited by nitric oxide. Endothelial cells appear to secrete short-lived endothelium-derived relaxing factors (EDRF), including nitric oxide or a related substance (Palmer et al. (1987) Nature 327: 524-526), when stimulated by vasoactive agents, such as acetylcholine and bradykinin. ET-induced vasoconstriction also is attenuated by atrial natriuretic peptide (ANP).

The ET peptides exhibit numerous biological activities in vitro and in vivo. ET provokes a strong and sustained vasoconstriction in vivo in rats and in isolated vascular smooth muscle preparations; it also provokes the release of eicosanoids and endothelium-derived relaxing factor (EDRF)

from perfused vascular beds. Intravenous administration of ET-1 and in vitro addition to vascular and other smooth muscle tissues produce long-lasting pressor effects and contraction, respectively (see, E., Bolger et al. (1991) Can. J. Physiol. Pharmacol. 69: 406-413). In isolated vascular strips, for example, ET-1 is a potent ($EC_{50}=4\times10^{-10}$ M), slow acting, but persistent, contractile agent. In vivo, a single dose elevates blood pressure in about twenty to thirty minutes. ET-induced vasoconstriction is not affected by antagonists to known neurotransmitters or hormonal factors, but is abolished by calcium channel antagonists. The effect of calcium channel antagonists, however, is most likely the result of inhibition of calcium influx, since calcium influx appears to be required for the long lasting contractile response to ET.

ET-1, which also is secreted by keratinocytes, stimulates proliferation, chemotaxis and pigment production in melanocytes and melanoma cells. G. Imokawa, et al., *Biochem. J.*, 314:305-12 (1996). Moreover, ultraviolet irradiation (UVR), which is implicated in melanoma development, induces a marked increase of ET-1 secretion by keratinocytes. G. Imokawa, et al., *J. Biol. Chem.*, 267; 24675-80 (1992).

ET also mediates renin release and induces a positive inotropic action in guinea pig atria. In the lung, ET-1 acts as a potent bronchoconstrictor (Maggi et al. (1989) Eur. J. Pharmacol. 160: 179-182). ET increases renal vascular resistance, decreases renal blood flow and decreases glomerular filtrate rate. It is a potent mitogen for glomerular mesangial cells and invokes the phosphoinoside cascade in such cells (Simonson et al. (1990) J. Clin. Invest. 85: 790-797).

There are specific high affinity binding sites (dissociation constants in the range of $2\text{-}6\times10^{-10}$ M) for the ETs in the vascular system and in other tissues, including the intestine, heart, lungs, kidneys, spleen, adrenal glands and brain. Binding is not inhibited by catecholamines, vasoactive peptides, neurotoxins or calcium channel antagonists. ET binds and interacts with receptor sites that are distinct from other autonomic receptors and voltage dependent calcium channels. Competitive binding studies indicate that there are multiple classes of receptors with different affinities for the ET isopeptides. The sarafotoxins, a group of peptide toxins from the venom of the snake Atractaspis eingadensis that cause severe coronary vasospasm in snake bite victims, have structural and functional homology to ET-1 and bind competitively to the same cardiac membrane receptors (Kloog et al. (1989) Trends Pharmacol. Sci. 10: 212-214).

Two distinct ET receptors, designated ETA and ETB, have been identified and DNA clones encoding each receptor have been isolated (Arai et al. (1990) Nature 348: 730-732; Sakurai et al. (1990) Nature 348: 732-735). Based on the amino acid sequences of the proteins encoded by the cloned DNA, it appears that each receptor contains seven membrane spanning domains and exhibits structural similarity to G-protein-coupled membrane proteins. Messenger RNA encoding both receptors has been detected in a variety of tissues, including heart, lung, kidney and brain. ET-1 binds with equal affinity to both ET receptors. H. Y. Kang, et al., *Pfiugers Arch.*, 435: 350-6 (1998).

The distribution of receptor subtypes is tissue specific (Martin et al. (1989) Biochem. Biophys. Res. Commun. 162: 130-137). ETA receptors appear to be selective for L. ET-1 and are predominant in cardiovascular tissues. ETB receptors are predominant in noncardiovascular tissues, including the central nervous system and kidney, and interact with the three ET isopeptides (Sakurai et al. (1990) Nature 348: 732-734). In addition, ETA receptors occur on vascular smooth muscle, are linked to vasoconstriction and have been associated with cardiovascular, renal and central nervous system diseases; whereas ETB receptors are located on the vascular endothelium, linked to vasodilation (Takayanagi et al. (1991) FEBS Lttrs. 282: 103-106) and have been associated with bronchoconstrictive disorders. Moreover, both ET receptors are expressed by melanocytes, while most melanomas express only ETB.

By virtue of the distribution of receptor types and the differential affinity of each isopeptide for each receptor type, the activity of the ET isopeptides varies in different tissues. For example, ET-1 inhibits $^{125}$I-labeled ET-1 binding in cardiovascular tissues forty to seven hundred times more potently than ET-3. $^{125}$I-labeled ET-1 binding in non-cardiovascular tissues, such as kidney, adrenal gland, and cerebellum, is inhibited to the same extent by ET-1 and ET-3, which indicates that ETA receptors predominate in cardiovascular tissues and ETB receptors predominate in non-cardiovascular tissues.

ET plasma levels are elevated in certain disease states (see, e.g., International PCT application WO 94/27979, and U.S. Pat. No. 5,382,569). ET-1 plasma levels in healthy individuals, as measured by radioimmunoassay (RIA), are about 0.26-5 pg/ml. Blood levels of ET-1 and its precursor, big ET, are elevated in shock, myocardial infarction, vasospastic angina, kidney failure and a variety of connective tissue disorders. In patients undergoing hemodialysis or kidney transplantation or suffering from cardiogenic shock, myocardial infarction or pulmonary hypertension levels as high as 35 pg/ml have been observed (see, Stewart et al. (1991) Annals Internal Med. 114: 464-469). Because ET is likely to be a local, rather than a systemic, regulating factor, it is probable that the levels of ET at the endothelium-smooth muscle interface are much higher than circulating levels.

Elevated levels of ET also have been measured in patients suffering from ischemic heart disease (Yasuda et al. (1990) Amer. Heart J. 119:801-806, Ray et al. (1992) Br. Heart J. 67:383-386). Circulating and tissue ET immunoreactivity is increased more than twofold in patients with advanced atherosclerosis (Lerman et al. (1991) New Engl. J. Med. 325: 997-1001). Increased ET immunoreactivity also has been associated with Buerger's disease (Kanno et al. (1990) J. Amer. Med. Assoc. 264:2868) and Raynaud's phenomenon (Zamora et al. (1990) Lancet 336 1144-1147). Increased circulating ET levels were observed in patients who underwent percutaneous transluminal coronary angioplasty (PTCA) (Tahara et al. (1991) Metab. Clin. Exp. 40:1235-1237; Sanjay et al. (1991) Circulation 84 (Suppl. 4):726), and in individuals (Miyauchi et al. (1992) Jpn. J. Pharmacol. 58:279 P; Stewart et al. (1991) Ann. Internal Medicine 114:464-469) with pulmonary hypertension.

2.2.1.1 Endothelin Agonists and Antagonists

Because ET is associated with certain disease states and is implicated in numerous physiological effects, compounds that can interfere with or potentiate ET-associated activities, such as ET-receptor interaction and vasoconstrictor activity, are of interest. Compounds that exhibit ET antagonistic activity have been identified. For example, a fermentation product of Streptomyces misakiensis, designated BE-18257B, has been identified as an ETA receptor antagonist. BE-18257B is a cyclic pentapeptide, cyclo(D-Glu-L-Ala-allo-D-lle-L-Leu-D-Trp), which inhibits $^{125}$I-labeled ET-1 binding in cardiovascular tissues in a concentration-dependent manner ($IC_{50}$ 1.4 µM in aortic smooth muscle, 0.8 µM in ventricle membranes and 0.5 µM in cultured aortic smooth muscle cells), but fails to inhibit binding to receptors in tissues in which ETB receptors predominate at concentrations up to 100 µM. Cyclic pentapeptides related to BE-18257B, such as cyclo(D-Asp-Pro-D-Val-Leu-D-Trp) (BQ-123), have been synthesized and shown to exhibit activity as ETA receptor antagonists (see, U.S. Pat. No. 5,114,918 to Ishikawa et al.; see, also, EP A10 436 189 to BANYU PHARMACEUTICAL CO., LTD (Oct. 7, 1991)). Studies that measure the inhibition by these cyclic peptides of ET-1 binding to ET-specific receptors indicate that these cyclic peptides bind preferentially to ETA receptors. Other peptide and non-peptidic ETA antagonists have been identified (see, e.g., U.S. Pat. Nos. 5,352,800, 5,334, 598, 5,352,659, 5,248,807, 5,240,910, 5,198,548, 5,187,195, 5,082,838). These include other cyclic pentapeptides, acyl-tripeptides, hexapeptide analogs, certain antraquinone derivatives, indanecarboxylic acids, certain N-pyriminylbenzenesulfonamides, certain benzenesulfonamides and certain naphthalenesulfonamides (Nakajima et al. (1991) J. Antibiot. 44:1348-1356; Miyata et al. (1992) J. Antibiot. 45:74-8; Ishikawa et al. (1992) J. Med. Chem. 35:2139-2142; U.S. Pat. No. 5,114,918 to Ishikawa et al.; EP A10 569 193; EP A1 0 558 258; EP A1 0 436 189 to BANYU PHARMACEUTICAL CO., LTD (Oct. 7, 1991); Canadian Patent Application 2,067, 288; Canadian Patent Application 2,071,193; U.S. Pat. No. 5,208,243; U.S. Pat. No. 5,270,313; U.S. Pat. No. 5,464,853; Cody et al. (1993) Med. Chem. Res. 3:154-162; Miyata et al. (1992) J. Antibiot 45:1041-1046; Miyata et al. (1992) J. Antibiot 45:1029-1040, Fujimoto et al. (1992) FEBS Lett. 305: 41-44; Oshashi et al. (1002) J. Antibiot 45:1684-1685; EP A10 496 452; Clozel et al. (1993) Nature 365:759-761; International Patent application WO93/08799; Nishikibe et al (1993) Life Sci. 52:717-724; and Benigni et al. (1993) Kidney Int. 44:440-444). In general, the identified compounds have activities in in vitro assays as ETA antagonists at concentrations on the order of about 50-100 μM or less. A number of such compounds have also been shown to possess activity in in vivo animal models. Very few selective ETB antagonists have been identified.

2.2.1.2 Endothelin Antagonists and Agonists as Therapeutic Agents

It has been recognized that compounds that exhibit activity at $IC_{50}$ or $EC_{50}$ concentrations on the order of $10^{-4}$ or lower in standard in vitro assays that assess ET antagonist or agonist activity have pharmacological utility (see, e., U.S. Pat. Nos. 5,352,800, 5,334,598, 5,352,659, 5,248,807, 5,240,910, 5,198,548, 5,187,195, 5,082,838). By virtue of this activity, such compounds are considered to be useful for the treatment of hypertension such as peripheral circulatory failure, heart disease such as angina pectoris, cardiomyopathy, arteriosclerosis, myocardial infarction, pulmonary hypertension, vasospasm, vascular restenosis, Raynaud's disease, cerebral stroke such as cerebral arterial spasm, cerebral ischemia, late phase cerebral spasm after subarachnoid hemorrhage, asthma, bronchoconstriction, renal failure, particularly post-ischemic renal failure, cyclosporine nephrotoxicity such as acute renal failure, colitis, as well as other inflammatory diseases, endotoxic shock caused by or associated with ET, and other diseases in which ET has been implicated.

In view of the numerous physiological effects of ET and its association with certain diseases, ET is believed to play a critical role in these pathophysiological conditions (see, e., Saito et al. (1990) Hypertension 15: 734-738; Tomita et al. (1989) N. Engl. J. Med. 321: 1127; Kurihara et al. (1989) J. Cardiovasc. Pharmacol. 13(Suppl. 5): S 13-S 17; Doherty (1992) J. Med. Chem. 35: 1493-1508; Morel et al. (1989) Eur. J. Pharmacol. 167: 427-428). More detailed knowledge of the function and structure of the ET peptide family should provide insight in the progression and treatment of such conditions.

To aid in gaining further understanding of and to develop treatments for ET-mediated or related disorders, there is a need to identify compounds that modulate or alter ET activity. Identification of compounds that modulate ET activity, such as those that act as specific antagonists or agonists, may not only aid in elucidating the function of ET, but may yield therapeutically useful compounds. In particular, compounds that specifically interfere with the interaction of ET peptides with the ETA or ETB receptors should be useful in identifying essential characteristics of ET peptides, should aid in the design of therapeutic agents and may be useful as disease specific therapeutic agents.

2.2.2 Cadherins

In vivo, cell-cell adhesion plays an important role in a wide range of events including morphogenesis and organ formation, modulation of the immune system, the formation of cell junctions and tumor metastasis and invasion. Additionally, cell-cell adhesion is crucial for the maintenance of tissue integrity, e.g., of the intestinal epithelial barrier, of the blood brain barrier and of cardiac muscle.

Intercellular adhesion is mediated by specific cell adhesion molecules. Cell adhesion molecules have been classified into at least three superfamilies including the immunoglobulin (Ig) superfamily, the integrin superfamily and the cadherin superfamily. All cell types that form solid tissues express some members of the cadherin superfamily suggesting that cadherins are involved in selective adhesion of most cell types.

Cadherins have been described generally as glycosylated integral membrane proteins that have an N-terminal extracellular domain that determines binding specificity (the N-terminal 113 amino acids appear to be directly involved in binding), a hydrophobic membrane-spanning domain and a C-terminal cytoplasmic domain (highly conserved among the members of the superfamily) that interacts with the cytoskeleton through catenins and other cytoskeleton-associated proteins. Some cadherins lack a cytoplasmic domain, however, and appear to function in cell-cell adhesion by a different mechanism than cadherins that do have a cytoplasmic domain. The cytoplasmic domain is required for the binding function of the extracellular domain in cadherins that do have a cytoplasmic domain. Binding between members of the cadherin family expressed on different cells is mainly homophilic (i.e., a member of the cadherin family binds to cadherins of its own or a closely related subclass) and $Ca^{2+}$-dependent.

The first cadherins to be described (E-cadherin in mouse epithelial cells, L-CAM in avian liver, uvomorulin in the mouse blastocyst, and CAM 120/80 in human epithelial cells) were identified by their involvement in $Ca^{2+}$-dependent cell adhesion and by their unique immunological characteristics and tissue localization. With the later immunological identification of N-cadherin, which was found to have a different tissue distribution from E-cadherin, it became apparent that a new family of $Ca^{2+}$-dependent cell-cell adhesion molecules had been discovered.

The molecular cloning of the genes encoding mouse E—(see Nagafuchi et al., Nature, 329: 341-343 (1987)), chicken—(Hatta et al., J. Cell Biol., 106: 873-881 (1988)), and mouse P—(Nose et al., EMBO J. 6: 3655-3661 (1987)) cadherins provided structural evidence that the cadherins comprised a family of cell adhesion molecules. Cloning of chicken L-CAM (Gallin et al., Proc. Natl. Acad. Sci. USA, 84: 2808-2812 (1987)) and mouse uvomorulin (Ringwald et al., EMBO J., 6: 3647-3653 (1987)) revealed that they were identical to E-cadherin. Comparisons of the amino acid sequences of E-, N-, and P-cadherins showed a level of amino acid similarity of about 45%-58% among the three subclasses.

The determination of the tissue expression of the various cadherins reveals that each subclass of cadherins has a unique tissue distribution pattern. For example, E-cadherin is found in epithelial tissues while N-cadherin is found in nonepithelial tissues such as neural and muscle tissue. The unique expression pattern of the different cadherins is particularly significant when the role each subclass of cadherins may play in vivo in normal events (e.g., the maintenance of the intestinal epithelial barrier) and in abnormal events (e.g., tumor metastasis or inflammation) is considered.

Suppression of cadherin function also has been implicated in the progression of various cancers. See Shimoyama et al., Cancer Res., 52: 5770-5774 (1992). In fact, E-cadherin has been shown to be a tumor invasion suppressor. M. Y. Hsu, et al., *J. Investig. Dermatol. Symp. Proc.*, 1:188-94 (1996). Furthermore, loss of E-cadherin (membrane associated) expression was found to be correlated with: lymph node metastasis of squamous cell carcinoma (J. H. Schipper, et al., Cancer Research 1991, 51: 6328-6337); dedifferentiation of meningiomas (Y. Tohma, et al., Cancer Research, 1992, 52: 1981-1987); high Gleason grade of prostate carcinomas (R. Umbas, et al., Cancer Research, 1992, 52: 5104-5109); infiltrative growth of basal cell carcinoma (A. Pizarro, et al. Br. J Cancer, 1994, 69: 157-162); dedifferentiation and metastasis of breast carcinoma (C. Gamallo, et al., American Journal of Pathology, 1993, 142: 987-993; R. Moll, et al., American Journal of Pathology, 1993, 143: 1731-1742; H. Oka, et al., Cancer Research, 1993, 53: 1696-1701); dedifferentiation, high Dukes stage and metastasis of colon carcinoma (S. Dorudi, et al., American Journal of Pathology, 1993, 142: 981-986; A. R. Kinsela, et al., Cancer Research, 1994, 67: 904-909); poor prognosis of bladder cancer (in combination with gp78) (T. Otto, et al., Cancer Research, 1994, 54: 3120-3123); dedifferentiation of thyroid carcinoma (C. Brabant, et al., cancer Research, 1993, 53: 4987-4993); and lymph node metastasis, high grade and advanced stage of pancreatic carcinoma (M. Pignatelli, et al., Journal of Pathology, 1994, 174: 243-248).

Recently, it has been shown that E-cadherin is expressed on cultured melanocytes where it mediates adhesion to keratinocytes. Danen et al., 1996, *Mel. Res.*, 6:127-131. Loss of contact with keratinocytes causes melanocytes to dedifferentiate and to express melanoma-associated cell-surface antigens. I. M. Shih, et al, *Am. J. Pathol.*, 145:837-45 (1994). Further, the acquisition of invasiveness of melanocytes is almost always accompanied by the down-regulation of E-cadherin. Moreover, the expression of E-cadherin is reduced in most melanoma cell lines. Thus, E-cadherin mediated cell contact between melanocytes and keratinocytes may be critical for the maintenance of normal melanocyte phenotype.

2.2.2.1 Catenins

The catenins have been classified into $\alpha$, $\beta$ and $\gamma$ on the basis of their electrophoretic mobilities (The EMBO Journal, 8, p 1711-1717 (1989)). Catenins are cytoplasmic proteins that are critical for E-cadherin function in cellular adhesion. J. M. Daniel, et al., *Bioessays*, 19:883-91 (1997). They bind to the cytoplasmic region of cadherins and function to modulate adhesion and/or bridge cadherins to the actin cytoskeleton. The catenins transmit an adhesion signal and anchor the cadherin to the actin cytoskeleton. The classical cadherins, E, N and P, bind directly to $\beta$-catenin. These, in turn, associate with the vinculin-like protein $\alpha$-catenin, which is thought to link cadherin complexes to the actin cytoskeleton, either by direct interaction or indirectly via $\alpha$-actinin. Daniel et al., 1997, *BioEssays*, 19(10): 883-891. Thus, disruption of the cadherin/catenin function could be integral to numerous diseases associated with a decrease in cadherin binding.

2.2.2.2 Caspases

Caspases, which are proteases best known for their role in apoptotic cell death, also are known to participate in inflammatory processes. Several studies recently have shown that proteases belonging to the caspase family are capable of cleaving $\beta$-catenin with a concomitant down-regulation of E-cadherin.

Caspases are activated in a sequential cascade beginning with apical caspases, such as caspase-8, which then activate distal caspases, such as caspases-3 and 7, which execute apoptotic cell death through cleavage of a variety of critical cell substrates. Caspase-8 may directly cleave catenin proteins or activate other as of yet unidentified caspase(s) which cleave catenin proteins, and this cleavage likely leads to destabilization and disruption of E-cadherin:catenin complexes at the plasma membrane. Indeed, caspase cleavage has been shown to prevent interaction of $\beta$-catenin with $\alpha$-catenin, the latter of which serves to anchor the E-cadherin:catenin complex to the actin cytoskeleton.

Thus, caspase activation may play a role in the down-regulation and destabilization of cadherin:catenin complexes. Moreover, as discussed above, down-regulation of cadherin-catenin complexes may play a role in the progression of various cancers.

3 SUMMARY OF THE INVENTION

The present invention relates to the treatment and prevention of cancer. More specifically, the present invention relates to the treatment and prevention of cancers including, but not limited to, melanoma, prostate cancer, colon cancer, ovarian cancer and mammary cancers using compositions which can be used as therapeutic agents which are capable of selectively inhibiting the early events that are associated with cancer development. The present invention further relates to methods for using the therapeutic compositions.

The invention is based, in part, on the Applicants' surprising discovery that the 21 amino acid peptide ET-1, which is synthesized and secreted by keratinocytes in response to ultraviolet radiation (UVR), and its receptor on melanocytes known as endothelin B receptor (ETB), are key components that initiate development of cancer, and specifically, melanoma. The Applicants' data presented herein demonstrate that blocking ETB with antagonists, or inactive forms of ET-1, inhibit the early events associated with melanoma development.

In particular, the working examples, infra., demonstrate that ET-1 down-regulates E-cadherin, p120$^{CTN}$ and $\beta$-catenin proteins in melanocytes and melanoma cells through activation of ETB. The data also demonstrates that ET-1 transiently activates caspase-8 and that inhibition of caspase-8 activity blocks the down-regulation of E-cadherin and catenin proteins by ET-1. Moreover, the working examples show that ET-1 fails to activate caspases-3 and 7 and does not induce apoptosis, but does, however, induce gross morphological alteration of melanocytes and loss of normal cell:cell contacts. Finally, the examples demonstrate that UVR induced ET-1 expression in keratinocytes promotes the development of UVR-induced melanocytic neoplasms through down-regulation of E-cadherin, a tumor invasion suppressor.

The present invention encompasses a variety of methods and compounds to target the activities of ETB. In particular, these include, but are not limited to, ETB antagonists and inactive peptide forms of ET-1 (ET-1 mimics), which would bind to ETB, but would not activate the receptor to initiate the cascade that leads to the early events associated with melanoma development. The invention encompasses known ETB antagonists and ET-1 mimics. Examples of such compounds include, but are not limited to, all protein compositions, SELEX RNAs, small molecule inhibitors, antisense molecules and ribozymes. Specific known ETB antagonists include, but are not limited to, IRL-1038 (Urade et al., 1992, FEBS Lett., 311:12-16), BQ788 (Karaki et al., 1994, Biochem. Biophys. Res. Commun., 205:168-173), RES-701-1 (Kohzuma et al., 1994, Neuroreport, 5:2653-2656), PD-142893 (Nishiyama et al., 1995, J. Pharmacol., Japan 69:391) and H-3596 (Shibata et al., 1996, Peptide Chemistry 1995, Proc. of the 33$^{rd}$ Symp. on Peptide Chem., Sapporo, Japan, page 281). Examples of ET-1 mimics include, but are not limited to, [Ala$^{3,11,18}$, Nle$^7$]-ET-1 (Hunt et al., 1991, Biorganic and Medic. Chem. Lett., 1:33), ET-1 (1'-21) (Urade et al., 1992, FEBS Lett., 311:12), cyclo (-Gly-Asn-Trp-His-Gly-Thr-Ala-Pro-β-Asp)-Trp-Phe-Phe-Asn-Tyr-Tyr-Trp-OH (Tanaka et al., 1994, Mol. Pharmacol., 45:724 and cyclo (-Gly-Asn-Trp-His-Gly-Thr-Ala-Pro-p-Asp)-Trp-Val-Tyr-Phe-Ala-His-Leu-Asp-Ile-Ile-Trp-OH (Shibata et al., 1996, Peptide Chemistry 1995, Proc. of the 33$^{rd}$ Symp. on Peptide Chem., Sapporo, Japan, page 281).

The present invention also relates to inhibitors of downstream effectors of compounds that are involved in the cascade leading to melanoma. Examples of such effectors are the caspases, catenins and cadherins. Examples of such compounds include, but are not limited to, all protein compositions, SELEX RNAs, small molecule inhibitors, antisense molecules, ribozymes, peptides and protease blockers. Specific known caspase inhibitors include, but are not limited to, any peptides or proteins with the following sequences: (a) IETD, (b) DEVD, (c) AEVD, (d) WEHD, (e) VAD and (f) FLIPs (Scaffidi et al., 1999, J. Biol. Chem., 3:1541-1548).

In another embodiment of the invention, gene therapy approaches may be used to practice the invention. While any number of DNA sequences can be used in the methods and compositions of the present invention, preferred DNA sequences are those that encode translational products (i.e. proteins) or transcriptional products (i.e. antisense or ribozymes) that (a) inhibit the ETB or (b) are capable of disrupting the progression of initiation of cancer (i.e. melanoma). For example, the DNA may comprise genes encoding therapeutically useful proteins such as growth factors, cytokines, hormones, etc. Additionally, the DNA may encode antisense or ribozyme molecules that may inhibit the translation of mRNAs encoding proteins that are involved in the initiation of cancer. In another embodiment of the invention, upstream and downstream effectors that are involved in the cascade leading to melanoma may be targeted by gene therapy approaches to inhibit cancer.

The present invention further relates to antibodies that specifically recognize one or more epitopes of ETB or ET-1. The present invention also relates to antibodies that specifically recognize effector compounds that are critical to the cascade leading to the cancer development.

The present invention further relates to screening assays to identify compounds which inhibit ETB activation and/or effectors that are critical to the cascade leading to cancer initiation or metastasis.

The invention is illustrated by way of working examples which demonstrate that ET-1 and ETB are key components that initiate the development of melanoma. The working examples of the invention also demonstrate the cascade of events which lead up to the development of melanoma. The working examples of the present invention further demonstrate the ability of inhibitors of ETB activation to inhibit the early events associated with melanoma development.

3.1 Definitions

As used herein, the term "melanoma" includes, but is not limited to, melanomas, malignant melanomas, metastatic melanomas, melanomas derived from either melanocytes or melanocytes related nevus cells, melanocarcinomas, melanoepitheliomas, melanosarcomas, amelanotic melanomas, desmoplastic malignant melanomas, halo melanomas, melanomas in situ, superficial spreading melanomas, nodular melanomas, malignant lentigo melanomas, acral lentiginous melanomas, subungual melanomas, minimal deviation melanomas, invasive melanomas or familial atypical mole and melanoma (FAM-M) syndrome. Such melanomas in mammals may be caused by chromosomal abnormalities, degenerative growth and developmental disorders, mitogenic agents, ultraviolet radiation (UVR), viral infections, inappropriate tissue expression of a gene, alterations in expression of a gene, and presentation on a cell or carcinogenic agents. The aforementioned melanomas can be diagnosed, assessed or treated by methods described in the present application.

As used herein, the term "atypical mole" refers to a mole with features that are abnormal and may be precancerous.

As used herein, the term "to target" means to inhibit, block, or prevent gene expression, enzymatic activity, or interaction with other cellular or viral factors or contain a deletion or mutation in the catalytic or enzymatic portion of the target protein.

As used herein, the term "dominant-negative mutant" means those proteins or polypeptides which are functionally incompetent forms of the target protein and/or inhibit or modulate the enzymatic activity of the target protein or inhibit or modulate the interaction of the target protein with other cellular or viral factors.

As used herein, the term "therapeutic agent" refers to any molecule, compound or treatment that can be used to prevent and/or treat cancer.

As used herein, the term "pharmaceutically acceptable carrier" refers to a carrier medium that does not interfere with the effectiveness of the biological activity of the active ingredient, is chemically inert and is not toxic to the patient to whom it is administered.

4 BRIEF DESCRIPTION OF THE DRAWINGS

The following drawings form part of the present specification and are included to further demonstrate certain aspects of the present invention. The invention may be understood better by reference to one or more of these drawings in combination with the detailed description of specific embodiments presented herein.

FIG. 1: Down-regulation of E-cadherin by ET-1. Lysates normalized for protein content were analyzed for E-cadherin protein levels by immunoblot analysis. (A) Stimulation of cells with 10 nM ET-1 over a 40 hour time course. Unstimulated controls are in first lanes of upper and lower panels. (B) Down-regulation of E-cadherin by ET-1 in other melanocyte and melanoma cell lines. (C) Effect of ET receptor antagonists. Cells were stimulated for 40 hours with 10 nM ET-1 and incubated with ETA antagonist BQ123 or ETB antagonist BQ788 as indicated. (D) Dose response. Cells were stimulated for 40 hours with: no ET-1, 0.5 nM ET-1, 1.0 nM ET-1, 10 nM ET-1 and 10 nM ET-3 lanes 1-5 respectively.

FIG. 2: Down-regulation of β-catenin and p120$^{CTN}$ by ET-1. Lysates normalized for protein content were analyzed for β-catenin and p120$^{CTN}$ protein levels by immunoblot analysis. Cells were stimulated with ET-1 as described previously. (A) β-catenin. (B) Effect of ET receptor antagonists. (C) p120$^{CTN}$.

FIG. 3: Caspase-8 activation by ET-1. (A) Inhibition of caspase-8 blocks down-regulation of E-cadherin by ET-1. SKMEL28 cells were treated with a variety of caspase inhibitors at the indicated concentrations. Samples were analyzed for E-cadherin protein levels as described previously. (B) Inhibition of caspase-8 blocks down-regulation of E-cadherin, β-catenin and p120$^{CTN}$ in FM2030 cells. Caspase-8 inhibition also blocked down-regulation of β-catenin and p120$^{CTN}$ in SKMEL28 cells. (C) ET-1 activates caspase-8. Upper panel: crude cytoplasmic extracts were prepared from FM2030 cells at the indicated time points post-ET-1 stimulation and caspase-8 activation examined by immunoblot analysis. Similar results were obtained using SKMEL28 cells. Asterixes indicate positions of fragments induced by ET-1 stimulation. Lower panel: Crude membrane fractions corresponding to samples in the upper panel were examined for E-cadherin protein levels by immunoblot analysis. (D) ET-1 does not activate caspases-3 and 7. Results shown are from SKMEL28 cells. Identical results were obtained using FM2030 cells.

FIG. 4: ET-1 alters the subcellular localization of E-cadherin and β-catenin. Cells were incubated either with or without 10 nM ET-1 for 96 hours then fixed and stained with anti-E-cadherin or anti-β-catenin antibodies followed by anti-mouse-IgG-Cy3 antibodies. E-cadherin localization is shown for melanocytes either (A) without or (B) with ET-1 incubation and in melanoma cells either (C) without or (D) with ET-1 incubation. β-catenin localization is shown for melanoma cells either (E) without or (F) with ET-1 incubation and in melanocytes either (G) without or (H) with ET-1 incubation. Melanocyte cell morphology is shown by bright field micrographs of cells either (I) without or (J) with ET-1 incubation. Incubation of melanocytes and melanoma cells with secondary antibody alone revealed no background staining.

5 DETAILED DESCRIPTION OF THE INVENTION

The present invention relates to therapeutic protocols and pharmaceutical compositions designed to target ET-1 mediated initiation of cancer, and effectors of the cascade initiated by ET-1 that lead to cancer related disorders and diseases, such as melanoma, prostate cancer, colon cancer, ovarian cancer and mammary cancer.

The invention is based, in part, on the surprising discovery that ET-1, which is synthesized and secreted by keratinocytes in response to UVR, and its receptor ETB are key components in the molecular cascade involved in the development of cancer. Applicants have demonstrated that antagonists to ETB, or inactive peptide forms of ET-1, are capable of inhibiting the early events associated with the development of cancers such as melanoma.

The present invention encompasses a variety of protocols to treat or prevent cancer development, including but not limited to: (1) protocols which target and inhibit ET-1 expression or inhibit the essential activities of the ETB receptor; (2) protocols which target and inhibit upstream effectors of the cascade that lead to the early development of cancer; and (3) protocols which target and inhibit downstream effectors of the cascade that lead to the early development of cancer.

In particular, the present invention encompasses the use of known compounds which specifically inhibit the ETB receptor and thus, modulate activation of the cascade that leads to the early development of cancer. The present invention also encompasses the use of known compounds which mimic ET-1 and bind to, but do not activate, the ETB receptor, thereby inhibiting the cascade that leads to the early development of cancer.

The present invention also relates to gene therapy approaches, including the use of DNA sequences that encode translational products (i.e. proteins) or transcriptional products (i.e. antisense or ribozymes) that (a) inhibit the ETB or (b) are capable of disrupting the progression of initiation of cancer (i.e. melanoma). For example, the DNA may comprise genes encoding therapeutically useful proteins such as growth factors, cytokines, hormones, etc. Additionally, the DNA may encode anti-sense or ribozyme molecules that may inhibit the translation of mRNAs encoding proteins that are involved in the initiation of cancer. In another embodiment of the invention, upstream and downstream effectors that are involved in the cascade leading to melanoma may be targeted by gene therapy approaches to inhibit cancer.

The present invention further relates to cell-based and animal model-based screening assays to identify novel agents which inactivate and/or mimic ET-1. In addition, the present invention relates to screening assays to identify novel antagonists to ETB or to other upstream or downstream effector molecules which are involved in the cascade leading to the early event associated with cancer development.

The present invention further encompasses pharmaceutical compositions containing the novel agents described herein. The therapeutic modalities of the invention further encompass combination therapies in which an agent which interferes with the interaction and/or activation of ET-1 with the ETB receptor, and at least one other therapeutic agent are administered either concurrently, e.g., as an admixture, separately but simultaneously or concurrently; or sequentially, including cycling therapy. Cycling therapy involves the administration of a first therapeutic compound for a period of time and repeating this sequential administration, i.e., the cycle, in order to reduce the development of resistance to one of the therapies.

5.1 The Role of Endothelin-1 in Cancer Development

Endothelin-1 (ET-1), a 21 amino-acid peptide secreted at high levels in UV (ultraviolet)-irradiated skin, stimulates melanin production and proliferation of melanocytes. The present invention is based, in part, on the Applicants' discovery that ET-1 down-regulates E-cadherin, p120$^{CTN}$ and β-catenin proteins in melanocytes and melanoma cells through activation of the Endothelin B receptor (ET-B), and thereby initiates the early events associated with melanoma development. Applicants demonstrate that ET-1 transiently activates caspase-8 and that inhibition of caspase-8 activity blocks the down-regulation of E-cadherin and catenin proteins by ET-1. Applicants further show that, although ET-1 fails to activate caspases-3 and 7 and does not induce apoptosis, it does induce gross morphological alteration of melanocytes and loss of normal cell:cell contacts. Applicants further show that since E-cadherin is a tumor-invasion suppressor, ET-1 expression promotes the development of UV-induced melanocytic neoplasms through down-regulation of E-cadherin.

Melanocytes are the pigment producing cells of the epidermis which undergo malignant transformation in malignant melanoma. Through their numerous dendritic processes, melanocytes contact multiple keratinocytes, the predominant cell type of the epidermis. This keratinocyte:melanocyte contact is mediated by the adhesion molecule E-cadherin. In normal skin, melanocytes are restricted to the basal layer of the epidermis, however in malignant melanoma, melanoma cells grow throughout all layers of the epidermis as well as in the underlying dermis. This acquisition of invasiveness is almost always accompanied by the down-regulation of E-cadherin, which is a tumor invasion suppressor. Moreover, melanocyte dedifferentiation and expression of melanoma-associated cell-surface antigens is associated with the toss of contact with keratinocytes. Thus, the keratinocyte-derived factor ET-1 modulates cell-surface antigen expression in melanocytes and E-cadherin, by mediating cell contact with keratinocytes, is critical for the maintenance of normal melanocyte phenotype.

As noted above, ET-1 is a 21 amino-acid peptide secreted by keratinocytes which stimulates proliferation, chemotaxis and pigment production in melanocytes and melanoma cells. UVR (ultraviolet irradiation), which is implicated in melanoma development, induces a marked increase of ET-1 secretion by keratinocytes. In the working examples described herein, Applicants demonstrate that ET-1 stimulation affects the adhesion of E-cadherin in melanocytes and melanoma cells. Applicants further demonstrate that there is a marked decrease in E-cadherin protein levels in human neonatal melanocytes (FM2030) and human melanoma cells (SKMEL28) following stimulation by ET-1.

Applicants further demonstrate in the working examples described herein that the ET-1 induced down-regulation of E-cadherin operates through activation of the ETB receptor on melanocytes. Although there are two well characterized ET-1, receptors, ETA and ETB, only antagonists to ETB blocked E-cadherin down-regulation by ET-1 suggesting that ETB activation is required for this response to occur (FIG. 1C). Applicants also demonstrate that the down-regulation of E-cadherin by ET-1 is dose-responsive in both melanocytes and melanoma cells (FIG. 1D).

Figure 2B:
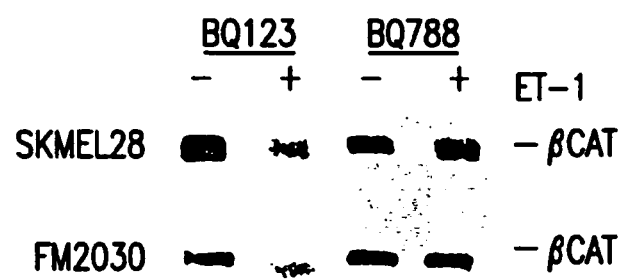
Figure 2C:
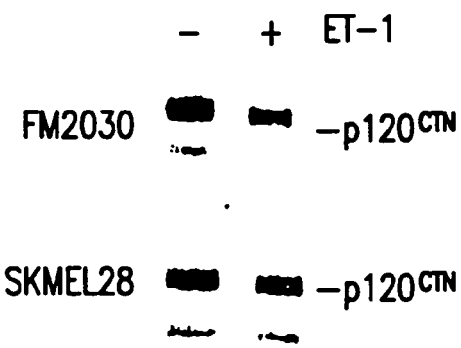

The Applicants have further demonstrated that catenins, which are cytoplasmic proteins that bind E-cadherin and are critical for E-cadherin function in cellular adhesion, in both melanocytes and melanoma cells, were down-regulated following stimulation by ET-1. More specifically, Applicants show that ET-1 stimulation decreased β-catenin protein levels and increased its electrophoretic mobility (FIG. 2A). The kinetics of this response also correlated well with those of E-cadherin down-regulation. Moreover, the examples described herein show that BQ788, a selective ETB antagonist, blocked the ET-1 mediated down-regulation of β-catenin (FIG. 2B). Thus, fhe down-regulation of both β-catenin and E-cadherin is mediated by ETB. ET-1 also down-regulated and increased the electrophoretic mobility of $p120^{CTN}$, another catenin family member, with kinetics paralleling those observed for E-cadherin and β-catenin down-regulation (FIG. 2C). Since, catenin proteins bind to cadherins and are critical for cadherin function in cellular adhesion, Applicants have shown for the first time that ET-1 stimulation of melanocytes and melanoma cells is associated with down-regulation of catenin proteins which induces a concomitant down-regulation of E-cadherin.

Applicants next demonstrate that the down-regulation of catenin proteins is regulated by caspases, which are proteases best known for their role in apoptotic cell death but also participate in inflammatory processes. More specifically, the examples described herein demonstrate that caspases are activated in response to ET-1 stimulation and participate in the down-regulation of E-cadherin, β-catenin and $p120^{CTN}$, without apoptosis. Further, inhibitors of caspase-8 processing blocked the down-regulation of E-cadherin, β-catenin and $p120^{CTN}$. Moreover, Applicants demonstrate that the time-points of maximal E-cadherin down-regulation coincide with the appearance of catalytically active caspase-8 subfragments (FIG. 3C, lower panel).

Although caspases are best known for their role in apoptosis, Applicants demonstrate that ET-1 induced caspase activation is not associated with apoptosis in melanocytes and melanoma cells. Caspases typically are activated in a sequential cascade beginning with apical caspases such as caspase-8 which then activate distal caspases such as caspases-3 and 7 which execute apoptotic cell death through cleavage of a variety of critical cell substrates. The apparent failure of ET-1 to activate distal caspases despite the activation of caspase-8 (FIG. 3D), is consistent with the failure to induce apoptosis in melanocytes and melanoma cells. If, however, the inhibition of apoptosis following ET-1 stimulation of melanocytes or melanoma cells could be overcome, the ET-1 stimulated melanocytes and melanoma cells would commit suicide. In order to overcome the inhibition of apoptosis, several approaches could be used. For example, and not by way of limitation, one could inhibit inhibitors of apoptosis (IAP's) using methods well known to those of skill in the art. In addition, since IAP expression is induced by activation of NF-κB, NF-κB activation could be inhibited by methods well known to those of skill in the art, such as by expressing I-κB, which is an inhibitor of NF-κB.

Thus, Applicants have demonstrated for the first time, E-cadherin and catenin down-regulation following ET-1 stimulation and E-cadherin and catenin down-regulation which is directly associated with ET-1 activation of caspases, without the concomitant induction of apoptosis. More specifically, ET-1 induces activation of caspase-8, which leads to the proteolysis of catenin proteins. This proteolysis of catenin proteins, which may explain the electrophoretic mobility shift of catenins following ET-1 stimulation, is associated with a concomitant down-regulation of E-cadherin. Finally, the down-regulation of E-cadherin is an early event associated with melanoma development. Therefore, Applicants have demonstrated that the early events associated with melanoma development, and cancer in general, can be inhibited by blocking either ETB with antagonists, or by using inactive peptide forms of ET-1, itself.

5.2 Treatment of Cancer Using Inhibitors of the Cascade Which Leads to Cancer Development The present invention encompasses a variety of therapeutic protocols, methods and compounds to prevent and/or treat cancer. These protocols, methods and compounds relate to ETB antagonists, ET-1 mimics and antagonists of downstream effector compounds, such as caspases, catenins and cadherins, that are involved in the cascade following ET-1 stimulation leading to melanoma development.

5.2.1 Compounds that Target ETB, Inhibit or Mimic ET-1 or Affect Effector Compounds Downstream in the Cascade Leading to Melanoma Development The Applicants have demonstrated that ETB is an essential component of the cascade that leads to the early events associated with Melanoma development. Further, the Applicants have demonstrated for the first time that antagonists of ETB, such as BQ788, are capable of blocking the cascade leading to melanoma development. There are a number of mechanisms by which ETB activation may be exerting its effects on the cascade leading to. melanoma development. The present invention encompasses both direct and indirect mechanisms by which the melanoma cascade may be blocked. For example, and not by way of limitation, an ETB antagonist may function by blocking the activation of a caspase, such as caspase-8. The lack of activation of caspase-8 would prevent the proteolysis of catenins, such as β-catenin. The intact β-catenin would then be capable of binding to cadherins, such as E-cadherin, which would promote th binding of keratinocytes to melanocytes. Thus, since E-cadherin levels decrease in melanoma, an ETB antagonist that blocks the activation of caspase also would block the early events associated with melanoma development.

In addition to the above-described mechanism for inhibiting the early events associated with melanoma development, other indirect mechanisms also are encompassed within the present invention. Such mechanisms might include, but are not limited to, antagonists of the mechanisms leading to: (a) caspase activation by ETB, (b) catenin proteolysis by caspase that specifically promotes caspase induction of apoptosis of melanocytes and melanoma cells via ET-1-ETB engagement or caspase-β-catenin activation, or (c),catenin mediated disruption of E-cadherin binding.

Examples of ETB antagonists which may be used in accordance with the present invention include, but are not limited to, all protein compositions, SELEX RNAs, small molecule inhibitors, antisense molecules and ribozymes. Specific known ETB antagonists include, but are not limited to, IRL-1038 (Urade et al., 1992, *FEBS Lett.*, 311:12-16), BQ788 (Karaki et al., 1994, *Biochem. Biophys. Res. Commun.*, 205: 168-173), RES-701-1 (Kohzuma et al., 1994, *Neuroreport*, 5:2653-2656), PD-142893 (Nishiyama et al., 1995, *J. Pharmacol.*, Japan 69:391) and H-3596 (Shibata et al., 1996, *Peptide Chemistry* 1995, *Proc. of the $33^{rd}$ Symp. on Peptide Chem.*, Sapporo, Japan, page 281).

In addition to ETB antagonists, inhibitors of ET-1 and mimics of ET-1 also are encompassed within the present invention. Inhibitors of ET-1 would reduce the levels of ET-1 within a cell, and, thus, would reduce the activation of the ETB receptor. Mimics of ET-1, however, would efficiently bind to ETB but they would not induce activation of the ETB receptor. Without activation of the ETB receptor, the cascade leading to the early events associated with melanoma development would be blocked.

Examples of ET-1 inhibitors and/or mimics which may be used in accordance with the present invention include, but are not limited to, [Ala$^{3,11,18}$, Nle$^7$]-ET-1 (Hunt et al., 1991, *Biorganic and Medic. Chem. Lett.*, 1:33), ET-1 (11-21) (Urade et al., 1992, *FEBS Lett.*, 311:12), cyclo (-Gly-Asn-Trp-His-Gly-Thr-Ala-Pro-β-Asp)-Trp-Phe-Phe-Asn-Tyr-Tyr-Trp-OH (Tanaka et al., 1994, *Mol. Pharmacol.*, 45:724 and cyclo (-Gly-Asn-Trp-His-Gly-Thr-Ala-Pro-β-Asp)-Trp-Val-Tyr-Phe-Ala-His-Leu-Asp-Ile-Ile-Trp-OH (Shibata et al., 1996, *Peptide Chemistry* 1995, *Proc. of the $33^{rd}$ Symp. on Peptide Chem.*, Sapporo, Japan, page 281).

Additional compounds which are encompassed within the present invention are any compounds which inhibit, either directly or indirectly, a compound that forms a key component of the cascade leading to melanoma development. Examples would be compounds that are capable of inhibiting caspase-8 activation, catenin proteolysis and cadherin binding properties. Examples of compounds which indirectly inhibit a compound that forms a key component of the cascade leading to melanoma development could be intermediate compounds that are involved in inhibiting caspase-8 activation, catenin proteolysis and cadherin binding properties, including compounds that have not yet been identified, but play key roles in the cascade.

Additional compounds that are encompassed within the invention include, but are not limited to, any compound which targets ETB and inhibits its activities, ET-1, caspase-8 and compounds which increase binding activities of catenins and cadherins, including, but not limited to dominant-negative mutants, antisense molecules and ribozymes. The present invention further relates to nucleotides, peptides, polypeptides, fusion proteins, antibodies and other-compounds which further modulate the above compounds and activities. Other examples of compounds include, but are not limited to, peptides or other compounds, including small organic and inorganic molecules directed to regions of the above compounds that are required either directly or indirectly for ETB activation or melanoma development.

5.3 Gene Therapy Approaches to Treat Melanoma Development

Gene therapy approaches also may be used in accordance with the present invention to inhibit the activation of ETB which induces the cascade leading to melanoma development. The gene therapy approaches described herein also may be applied to ET-1 and upstream and downstream effectors of the melanoma development cascade in accordance with the present invention. Among the compounds which may disrupt the activities of ETB and its activation of the melanoma development signaling cascade are antisense, ribozyme, triple helix molecules and dominant-negative mutants. Such molecules are designed to inhibit the expression of the target gene in host cells. Techniques for the production and use of antisense, ribozyme and/or triple helix molecules are well known to those of skill in the art and can be designed with respect to the cDNA sequence of ETB and components of the melanoma development cascade.

5.3.1 Nucleic Acids for Gene Therapy Approaches

Antisense RNA and DNA molecules act to directly block the translation of mRNA by hybridizing to targeted mRNA and preventing protein translation. Ribozymes are enzymatic RNA molecules capable of catalyzing the specific cleavage of RNA. (For a review see Rossi, J., 1994, *Current Biology* 4:469-471). The mechanism of ribozyme action involves sequence specific hybridization of the ribozyme molecule to complementary target RNA, followed by an endonucleolytic cleavage. The composition of ribozyme molecules must include one or more sequences complementary to the target gene mRNA, and must include the well known catalytic sequence responsible for mRNA cleavage. For this sequence, see U.S. Pat. No. 5,093,246, which is incorporated by reference in its entirety. As such, within the scope of the invention, are engineered hammerhead motif ribozyme molecules that specifically and efficiently catalyze endonucleolytic cleavage of RNA sequences encoding target gene proteins.

Specific ribozyme cleavage sites within any potential RNA target are initially identified by scanning the molecule of interest for ribozyme cleavage sites which include the following sequences: GUA, GUU and GUC. Once identified, short RNA sequences of between 15 and 20 ribonucleotides corresponding to the region of the target gene containing the cleavage site may be evaluated for predicted structural features, such as secondary structure, that may render the oligonucleotide sequence unsuitable. The suitability of candidate sequences may be evaluated also by testing their accessibility to hybridize with complementary oligonucleotides, using ribonuclease protection assays.

Nucleic acid molecules to be used in triple helix formation for the inhibition of transcription should be single stranded and composed of deoxynucleotides. The base composition of these oligonucleotides must be designed to promote triple helix formation via Hoogsteen base pairing rules, which generally require sizeable stretches of either purines or pyrimidines to be present on one strand of a duplex. Nucleotide sequences may be pyrimidine-based, which will result in TAT and CGC$^+$ triplets across the three associated strands of the resulting triple helix. The pyrimidine-rich molecules provide base complementarity to a purine-rich region of a single strand of the duplex in a parallel orientation to that strand. In addition, nucleic acid molecules may be chosen that are purine-rich, for example, contain a stretch of G residues.

These molecules will form a triple helix with a DNA duplex that is rich in GC pairs, in which the majority of the purine residues are located on a single strand of the targeted duplex, resulting in GGC triplets across the three strands in the triplex.

Alternatively, the potential sequences that can be targeted for triple helix formation may be increased by creating a so called "switchback" nucleic acid molecule. Switchback molecules are synthesized in an alternating 5'-3', 3'-5' manner, such that they base pair first with one strand of a duplex and then the other, eliminating the necessity for a sizeable stretch of either purines or pyrimidines to be present on one strand of a duplex.

In instances wherein the antisense, ribozyme, and/or triple helix molecules described herein are utilized to inhibit gene expression, it is possible that the technique may Ad so efficiently reduce or inhibit the transcription (triple helix) and/or translation (antisense, ribozyme) of mRNA produced by normal target gene alleles that the possibility may arise wherein the concentration of normal target gene product present may be lower than is necessary for a normal phenotype. In such cases, to ensure that substantially normal levels of target gene activity are maintained, therefore, nucleic acid molecules that encode and express target gene polypeptides exhibiting normal target gene activity may be introduced into cells via gene therapy methods such as those described, that do not contain sequences susceptible to whatever antisense, ribozyme or triple helix treatments are being utilized. Alternatively, in instances whereby the target gene encodes an extracellular protein, it may be preferable to co-administer normal target gene protein in order to maintain the requisite level of target gene activity.

Anti-sense RNA and DNA, ribozyme and triple helix molecules of the invention may be prepared by any method known in the art for the synthesis of DNA and RNA molecules. These include techniques for chemically synthesizing oligodeoxyribonucleotides and oligoribonucleotides well known in the art such as for example solid phase phosphoramidite chemical synthesis. Alternatively, RNA molecules may be generated by in vitro and in vivo transcription of DNA sequences encoding the antisense RNA molecule. Such DNA sequences may be incorporated into a wide variety of vectors which incorporate suitable RNA polymerase promoters such as the T7 or SP6 polymerase promoters. Alternatively, antisense cDNA constructs that synthesize antisense RNA constitutively or inducibly, depending on the promoter used, can be introduced stably into cell lines.

Various well-known modifications to the DNA molecules may be introduced as a means of increasing intracellular stability and half-life. Possible modifications include, but are not limited to, the addition of flanking sequences of ribo- or deoxy-nucleotides to the 5' and/or 3' ends of the molecule or the use of phosphorothioate or 2' O-methyl rather than phosphodiesterase linkages within the oligodeoxyribonucleotide backbone.

Nucleic acids encoding dominant-negative mutants of the invention may be prepared by any method known in the art for the synthesis of DNA and RNA molecules. The dominant-negative mutants of the present invention may be produced by recombinant DNA technology using techniques well known in the art. Methods which are well known to those skilled in the art can be used to construct expression vectors containing the dominant-negative mutant gene product coding sequences and appropriate transcriptional and translational control signals. These methods are described in more detail herein.

5.3.2 Delivery of Nucleic Acids

Delivery of the nucleic acid into a patient may be either direct, in which case the patient is directly exposed to the nucleic acid or nucleic acid-carrying vector, or indirect, in which case, cells are first transformed with the nucleic acid in vitro, then transplanted into the patient for cell replacement therapy. These two approaches are known, respectively, as in vivo or ex vivo gene therapy.

In a specific embodiment, the nucleic acid is directly administered in vivo, where it is expressed to produce the encoded product. This can be accomplished by any of numerous methods known in the art, e.g., by constructing it as part of an appropriate nucleic acid expression vector and administering it so that it becomes intracellular, e.g., by infection using a defective or attenuated retroviral or other viral vector (see U.S. Pat. No. 4,980,286), or by direct injection of naked DNA, or by use of microparticle bombardment (e.g., a gene gun; Biolistic, Dupont), or coating with lipids or cell-surface receptors or transfecting agents, encapsulation in liposomes, microparticles, or microcapsules, or by administering it in linkage to a peptide which is known to enter the cell or nucleus, e.g., by administering it in linkage to a ligand subject to receptor-mediated endocytosis (see e.g., Wu and Wu, 1987, J. Biol. Chem. 262:4429-4432) (which can be used to target cell types specifically expressing the receptors), etc. In a specific embodiment, the nucleic acid can be targeted in vivo for cell specific uptake and expression, by targeting a specific receptor (see, e.g., PCT Publications WO 92/06180 dated Apr. 16, 1992 (Wu et al.); WO 92/22635 dated Dec. 23, 1992 (Wilson et al.); WO92/20316 dated Nov. 26, 1992 (Findeis et al.); WO93/14188-dated Jul. 22, 1993 (Clarke et al.), WO 93/20221 dated Oct. 14, 1993 (Young)). In another embodiment, a nucleic acid-ligand complex can be formed in which the ligand comprises a fusogenic viral peptide to disrupt endosomes, allowing the nucleic acid to avoid lysosomal degradation. Alternatively, the nucleic acid can be introduced intracellularly and incorporated within host cell DNA for expression, by homologous recombination (Koller & Smithies, 1989, Proc. Natl. Acad. Sci. USA 86:8932-8935; Zijlstra et al., 1989, Nature 342:435-438).

In a specific embodiment, a viral vector that contains the gene promoter suppressing nucleic acid is used. For example, a retroviral vector can be used (see Miller et al., 1993, Meth. Enzymol. 217:581-599). These retroviral vectors have been modified to delete retroviral sequences that are not necessary for packaging of the viral genome. Retroviral vectors are maintained in infected cells by integration into genomic sites upon cell division. The nucleic acid to be used in gene therapy is cloned into the vector, which facilitates delivery of the gene into a patient. More detail about retroviral vectors can be found in Boesen et al., 1994, Biotherapy 6:291-302, which describes the use of a retroviral vector to deliver the mdr1 gene to hematopoietic stem cells in order to make the stem cells more resistant to chemotherapy. Other references illustrating the use of retroviral vectors in gene therapy are: Clowes et al., 1994, J. Clin. Invest. 93:644-651; Kiem et al., 1994, Blood 83:1467-1473; Salmons and Gunzberg, 1993, Human Gene Therapy 4:129-141; and Grossman and Wilson, 1993, Curr. Opin. in Genetics and Devel. 3:110-114.

Adenoviruses are other viral vectors that can be used in gene therapy. Adenoviruses are especially attractive vehicles for delivering genes to liver and respiratory epithelia. Adenoviruses naturally infect respiratory epithelia where they cause a mild disease. Other targets for adenovirus-based delivery systems are liver, the central nervous system, endothelial cells and muscle. Adenoviruses have the advantage of being capable of infecting non-dividing cells. Kozarsky and Wilson, 1993, Current Opinion in Genetics and Development 3:499-503 present a review of adenovirus-based gene therapy. Bout et al., 1994, Human Gene Therapy 5:3-10 demonstrated the use of adenovirus vectors to transfer genes to the respiratory epithelia of rhesus monkeys. Other instances of the use of adenoviruses in gene therapy can be found in Rosenfeld et al., 1991, Science 252:431-434; Rosenfeld et al., 1992, Cell 68:143-155; and Mastrangeli et al., 1993, J. Clin. Invest, 91:225-234.

Adeno-associated virus (AAV) also has been proposed for use in gene therapy (Walsh et al., 1993, Proc. Soc. Exp. Biol. Med. 204:289-300). Herpes viruses are other viruses that also can be used.

Another approach to gene therapy, for use in the cell replacement therapy of the invention, involves transferring a gene to cells in tissue culture by such methods as electroporation, lipofection, calcium phosphate mediated transfection or viral infection. Usually, the method of transfer includes the transfer of a selectable marker to the cells. The cells are then placed under selection to isolate those cells that have taken up and are expressing the transferred gene. Those cells are then delivered to a patient.

In this embodiment, the nucleic acid is introduced into a cell prior to administration in vivo of the resulting recombinant cell. Such introduction can be carried out by any method known in the art, including, but not limited to, transfection, electroporation, microinjection, infection with a viral vector containing the nucleic acid sequences, cell fusion, chromosome-mediated gene transfer, microcell-mediated gene transfer, spheroplast fusion, etc. Numerous techniques are known in the art for the introduction of foreign genes into cells (see e.g., Loeffler & Behr, 1993, Meth. Enzymol. 217:599-618; Cohen et al., 1993, Meth. Enzymol. 217:618-644; Cline, 1985, Pharmac. Ther. 29:69-92) and may be used in accordance with the present invention, provided that the necessary developmental and physiological functions of the recipient cells are not disrupted. The technique should provide for the stable transfer of the nucleic acid to the cell, so that the nucleic acid is expressible by the cell and preferably heritable and expressible by its cell progeny.

The resulting recombinant cells can be delivered to a patient by various methods known in the art. In a preferred embodiment, epithelial cells are injected, e.g., subcutaneously. In another embodiment, recombinant skin cells (e.g., keratinocytes) may be applied as a skin graft onto the patient. Recombinant blood cells (e.g., hematopoietic stem or progenitor cells) are preferably administered intravenously. The amount of cells envisioned for use depends on the desired effect, patient state, etc., and can be determined by one skilled in the art.

In an embodiment in which recombinant cells are used in gene therapy, nucleotides which encode a gene or promoter suppressor such as an inhibiting form of ET-1, ETB or pro-apoptotic molecule for caspase destruction of melanoma cells that are normally resistant to apoptosis, are introduced into the cells such that it is expressible by the cells or their progeny, and the recombinant cells are then administered in vivo for therapeutic effect. In a specific embodiment, stem or progenitor cells are used. Any stem and/or progenitor cells which can be isolated and maintained in vitro can potentially be used in accordance with this embodiment of the present invention.

5.4 Antibodies to Treat Melanoma Development

Antibodies that specifically recognize one or more epitopes of ETB, ET-1 or epitopes of effector compounds involved in the cascade leading to cancer development also are encompassed by the invention. Such antibodies include, but are not limited to, polyclonal antibodies, monoclonal antibodies (mAbs), humanized or chimeric antibodies, single chain antibodies, Fab fragments, F(ab')$_2$ fragments, fragments produced by a Fab expression library, anti-idiotypic (anti-Id) antibodies and epitope-binding fragments of any of the above.

For the production of antibodies, various host animals may be immunized by injection with ETB, ET-1 or effector compounds involved in the cascade leading to cancer development. In addition, functional domains, truncated portions and functional equivalents of these proteins may be used to immunize various host animals. Host animals may include, but are not limited to, rabbits, mice and rats, to name but a few. Various adjuvants may be used to increase the immunological response, depending on the host species, including, but not limited to, Freund's (complete and incomplete), mineral gels such as aluminum hydroxide, surface active substances such as lysolecithin, pluronic polyols, polyanions, peptides, oil emulsions, keyhole limpet hemocyanin, dinitrophenol and potentially useful human adjuvants such as BCG (bacille Calmette-Guerin) and *Corynebacterium parvum*. Polyclonal antibodies are heterogeneous populations of antibody molecules derived from the sera of the immunized animals.

Monoclonal antibodies, which are homogeneous populations of antibodies to a particular antigen, may be obtained by any technique which provides for the production of antibody molecules by continuous cell lines in culture. These include, but are not limited to, the hybridoma technique of Kohler and Milstein, (Nature 256:495-497 [1975]; and U.S. Pat. No. 4,376,110), the human B-cell hybridoma technique (Kosbor et al., 1983, Immunology Today 4:72; Cole et al., 1983, Proc. Natl. Acad. Sci. USA 80:2026-2030) and the EBV-hybridoma technique (Cole et al., 1985, Monoclonal Antibodies And Cancer Therapy, Alan R. Liss, Inc., pp. 77-96). Such antibodies may be of any immunoglobulin class including IgG, IgM, IgE, IgA, IgD and any subclass thereof. The hybridoma producing tL the mAb of this invention may be cultivated in vitro or in vivo. Production of high titers of mAbs in vivo makes this the presently preferred method of production.

In addition, techniques developed for the production of "chimeric antibodies" (Morrison et al., 1984, Proc. Natl. Acad. Sci., 81:6851-6855; Neuberger et al., 1984, Nature, 312:604-608; Takeda et al., 1985, Nature, 314:452-454) by splicing the genes from a mouse antibody molecule of appropriate antigen specificity together with genes from a human antibody molecule of appropriate biological activity can be used. A chimeric antibody is a molecule in which different portions are derived from different animal species, such as those having a variable region derived from a murine mAb and a human immunoglobulin constant region.

In addition, techniques have been developed for the production of humanized antibodies. (See, e.g., Queen, U.S. Pat. No. 5,585,089.) An immunoglobulin light or heavy chain variable region consists of a "framework" region interrupted by three hypervariable regions, referred to as complementarity determining regions (CDRs). The extent of the framework region and CDRs have been precisely defined (see, "Sequences of Proteins of Immunological Interest", Kabat, E. et al., U.S. Department of Health and Human Services (1983)). Briefly, humanized antibodies are antibody molecules from non-human species having one or more CDRs from the non-human species and a framework region from a human immunoglobulin molecule.

Alternatively, techniques described for the production of single chain antibodies (U.S. Pat. No. 4,946,778; Bird, 1988, Science 242:423-426; Huston et al., 1988, Proc. Natl. Acad. Sci. USA 85:5879-5883; and Ward et al., 1989, Nature 334:

544-546) can be adapted to produce single chain antibodies against ETB, ET-1 or effector compounds involved in the cascade leading to cancer development. Single chain antibodies are formed by linking the heavy and light chain fragments of the Fv region via an amino acid bridge, resulting in a single chain polypeptide.

Antibody fragments which recognize specific epitopes may be generated by known techniques. For example, such fragments include, but are not limited to: the $F(ab')_2$ fragments which can be produced by pepsin digestion of the antibody molecule and the Fab fragments which can be generated by reducing the disulfide bridges of the $F(ab')_2$ fragments. Alternatively, Fab expression libraries may be constructed (Huse et al., 1989, Science, 246:1275-1281) to allow rapid and easy identification of monoclonal Fab fragments with the desired specificity.

Antibodies to a ETB, ET-1 or effector compounds involved in the cascade leading to cancer development can, in turn, be utilized to generate anti-idiotype antibodies that "mimic" these compounds, using techniques well known to those skilled in the art. (See, e.g., Greenspan & Bona, 1993, FASEB J 7(5):437-444; and Nissonoff, 1991, J. Immunol. 147(8): 2429-2438).

5.5 Pharmaceutical Formulations and Methods of Administration

The present invention encompasses the use of known agents which block ETB activation and or inhibit ET-1 activity and novel agents identified by the screening methods of the invention in pharmaceutical compositions and therapeutic modalities for the treatment of melanomas. In one embodiment of the present invention, the novel agents identified by the screening assays of the present invention may be used in combination with other known agents to treat and/or prevent cancer.

5.5.1 Routes of Administration

Suitable routes of administration may, for example, include oral, rectal, transmucosal, or intestinal administration; parenteral delivery, including intramuscular, subcutaneous, intramedullary injections, as well as intrathecal, direct intraventricular, intravenous, intraperitoneal, intranasal, or intraocular injections, and optionally in a depot or sustained release formulation. Furthermore, one may administer the agent of the present invention in a targeted drug delivery system, for example in a liposome.

5.5.2 Composition/Formulation

The pharmaceutical compositions of the present invention may be manufactured in a manner that is itself known, e.g., by means of conventional mixing, dissolving, dragee-making, levitating, emulsifying, encapsulating, entrapping or lyophilizing processes.

Pharmaceutical compositions for use in accordance with the present invention thus may be formulated in conventional manner using one or more physiologically acceptable carriers comprising excipients and auxiliaries which facilitate processing of the active compounds into preparations which can be used pharmaceutically. Proper formulation is dependent upon the route of administration chosen.

For injection, the agents of the invention may be formulated in aqueous solutions, preferably in physiologically compatible buffers, such as Hank's solution, Ringer's solution or physiological saline buffer. For transmucosal administration, penetrants appropriate to the barrier to be permeated are used in the formulation. Such penetrants are usually known in the art.

For oral administration, the compounds can be formulated readily by combining the active compounds with pharmaceutically acceptable carriers well known to those in the art. Such carriers enable the compounds of the invention to be formulated as tablets, pills, dragees, capsules, liquids, gels, syrups, slurries, suspensions and the like, for oral ingestion by a patient to be treated. Pharmaceutical preparations for oral use can be obtained solid excipient, optionally grinding a resulting mixture, and processing the mixture of granules, after adding suitable auxiliaries, if desired, to obtain tablets or dragee cores. Suitable excipients are, in particular, fillers such as sugars, including lactose, sucrose, mannitol, or sorbitol; cellulose preparations such as, for example, maize starch, wheat starch, rice starch, potato starch, gelatin, gum tragacanth, methyl cellulose, hydroxypropylmethylcellulose, sodium carboxymethylcellulose, and/or polyvinylpyrrolidone (PVP). If desired, disintegrating agents may be added, such as the cross-linked polyvinyl pyrrolidone, agar, or alginic acid or a salt thereof such as sodium alginate.

Dragee cores are provided with suitable coatings. For this purpose, concentrated sugar solutions may be used, which may optionally contain gum arabic, talc, polyvinyl pyrrolidone, carbopol gel, polyethylene glycol, and/or titanium dioxide, lacquer solutions, and suitable organic solvents or solvent mixtures. Dyestuffs or pigments may be added to the tablets or dragee coatings for identification or to characterize different combinations of active compound doses.

Pharmaceutical preparations which can be used orally include push-fit capsules made of gelatin, as well as soft, sealed capsules made of gelatin and a plasticizer, such as glycerol or sorbitol. The push-fit capsules can contain the active ingredients in admixture with filler such as lactose, binders such as starches, and/or lubricants such as talc or magnesium stearate and, optionally, stabilizers. In soft capsules, the active compounds may be dissolved or suspended in suitable liquids, such as fatty oils, liquid paraffin, or liquid polyethylene glycols. In addition, stabilizers may be added. All formulations for oral administration should be in dosages suitable for such administration.

For buccal administration, the compositions may take the form of tablets or lozenges formulated in conventional manner.

For administration by inhalation, the compounds for use according to the present invention are conveniently delivered in the form of an aerosol spray presentation from pressurized packs or a nebulizer, with the use of a suitable propellant, e.g., dichlorodifluoromethane, trichlorofluoromethane, dichlorotetrafluoroethane, carbon dioxide or other suitable gas. In the case of a pressurized aerosol the dosage unit may be determined by providing a valve to deliver a metered amount. Capsules and cartridges of e.g. gelatin for use in an inhaler or insufflator may be formulated containing a powder mix of the compound and a suitable powder base such as lactose or starch.

The compounds may be formulated for parenteral administration by injection, e.g., by bolus injection or continuous infusion. Formulations for injection may be presented in unit dosage form, e.g., in ampoules or in multi-dose containers, with an added preservative. The compositions may take such forms as suspensions, solutions or emulsions in oily or aqueous vehicles, and may contain formulatory agents such as suspending, stabilizing and/or dispersing agents.

Pharmaceutical formulations for parenteral administration include aqueous solutions of the active compounds in water-soluble form. Additionally, suspensions of the active compounds may be prepared as appropriate oily injection suspensions. Suitable lipophilic solvents or vehicles include fatty oils such as sesame oil, or synthetic fatty acid esters, such as ethyl oleate or triglycerides, or liposomes. Aqueous injection suspensions may contain substances which increase the viscosity of the suspension, such as sodium carboxymethyl cellulose, sorbitol, or dextran. Optionally, the suspension may also contain suitable stabilizers or agents which increase the solubility of the compounds to allow for the preparation of highly concentrated solutions.

Alternatively, the active ingredient may be in powder form for constitution with a suitable vehicle, e.g., sterile pyrogen-free water, before use.

The compounds may also be formulated in rectal compositions such as suppositories or retention enemas, e.g., containing conventional suppository bases such as cocoa butter or other glycerides.

In addition to the formulations described previously, the compounds also may be formulated as a depot preparation. Such long acting formulations may be administered by implantation (for example subcutaneously or intramuscularly) or by intramuscular injection. Thus, for example, the compounds may be formulated with suitable polymeric or hydrophobic materials (for example as an emulsion in an acceptable oil) or ion exchange resins, or as sparingly soluble derivatives, for example, as a sparingly soluble salt.

Liposomes and emulsions are well known examples of delivery vehicles or carriers for hydrophobic drugs. Certain organic solvents such as dimethylsulfoxide also may be employed, although usually at the cost of greater toxicity. Additionally, the compounds may be delivered using a sustained-release system, such as semipermeable matrices of solid hydrophobic polymers containing the therapeutic agent. Various sustained-release materials have been established and are well known by those skilled in the art. Sustained-release capsules may, depending on their chemical nature, release the compounds for a few weeks up to over 100 days. Depending on the chemical nature and the biological stability of the therapeutic reagent, additional strategies for protein stabilization may be employed.

The pharmaceutical compositions also may comprise suitable solid or gel phase carriers or excipients. Examples of such carriers or excipients include but are not limited to calcium carbonate, calcium phosphate, various sugars, starches, cellulose derivatives, gelatin, and polymers such as polyethylene glycols.

Many of the compounds of the invention identified as inhibitors of the ETB may be provided as salts with pharmaceutically compatible counterions. Pharmaceutically compatible salts may be formed with many acids, including but not limited to hydrochloric, sulfuric, acetic, lactic, tartaric, malic, succinic, etc.; or bases. Salts tend to be more soluble in aqueous or other protonic solvents that are the corresponding free base forms. Examples of pharmaceutically acceptable salts, carriers or excipients are well known to those skilled in the art and can be found, for example, in *Remington's Pharmaceutical Sciences*, 18th Edition, A. R. Gennaro, Ed., Mack Publishing Co., Easton, Pa., 1990. Such salts include, but are not limited to, sodium, potassium, lithium, calcium, magnesium, iron, zinc, hydrochloride, hydrobromide, hydroiodide, acetate, citrate, tartrate, malate sales and the like.

5.5.3 Effective Dosage

Pharmaceutical compositions suitable for use in the present invention include compositions wherein the active ingredients are contained in an effective amount to achieve their intended purpose. More specifically, a therapeutically effective amount means an amount effective to prevent development of or to alleviate the existing symptoms of the subject being treated. Determination of the effective amounts is well within the capability of those skilled in the art, especially in light of the detailed disclosure provided herein.

For any compound used in the method of the invention, the therapeutically effective dose can be estimated initially from cell culture assays. Such information can be used to more accurately determine useful doses in humans.

A therapeutically effective dose refers to that amount of the compound that results in a reduction in the intensity of the infection or in amelioration of symptoms or a prolongation of survival in a patient. Toxicity and therapeutic efficacy of such compounds can be determined by standard pharmaceutical, pharmacological, and toxicological procedures in cell cultures or experimental animals, e.g., for determining the $LD_{50}$ (the dose lethal to 50% of the population) and the $ED_{50}$ (the dose therapeutically effective in 50% of the population). The dose ratio between toxic and therapeutic effects is the therapeutic index and it can be expressed as the ratio between $LD_{50}$ and $ED_{50}$. Compounds which exhibit high therapeutic indices are preferred. The data obtained from cell culture assays or animal studies can be used in formulating a range of dosage for use in humans. The dosage of such compounds lies preferably within a range of circulating concentrations that include the $ED_{50}$ with little or no toxicity. The dosage may vary within this range depending upon the dosage form employed and the route of administration utilized. The exact formulation, route of administration and dosage can be chosen by the individual physician in view of the patient's condition. (See e.g. Fingl et al., 1975, in "The Pharmacological Basis of Therapeutics", Ch. 1 p. 1).

Dosage amount and interval may be adjusted individually to provide plasma levels of the active moiety which are sufficient to maintain the desired modulating effects, or minimal effective concentration (MEC). The MEC will vary for each compound but can be estimated from in vitro data. Dosages necessary to achieve the MEC will depend on individual characteristics and route of administration. However, HPLC assays, bioassays or immunoassays can be used to determine plasma concentrations.

Dosage intervals also can be determined using the MEC value. Compounds should be administered using a regimen which maintains plasma levels above the MEC for 10-90% of the time, preferably between 30-90% and most preferably between 50-90%.

In cases of local administration or selective uptake, the effective local concentration of the drug may not be related to plasma concentration.

The amount of composition administered will, of course, be dependent on the subject being treated, on the subject's weight, the severity of the affliction, the manner of administration and the judgment of the prescribing physician.

In immunization procedures, the amount of immunogen to be used and the immunization schedule will be determined by a physician skilled in the art and will be administered by reference to the immune response and antibody titers of the subject.

5.5.4 Packaging

The compositions may, if desired, be presented in a pack or dispenser device which may contain one or more unit dosage forms containing the active ingredient. The pack may for example comprise metal or plastic foil, such as a blister pack. The pack or dispenser device may be accompanied by instructions for administration. Compositions comprising a compound of the invention formulated in a compatible pharmaceutical carrier also may be prepared, placed in an appropriate container and labeled for treatment of an indicated condition.

5.6 Screening Assays for Compounds that are Capable of Preventing or Treating Melanomas The following assays are designed to identify compounds that are capable of preventing and/or treating melanomas.

Such compounds can act as the basis for amelioration of cancers including melanoma, for example. Such compounds may include, but are not limited to, peptides, antibodies or small organic or inorganic compounds. Methods for the identification of such compounds are described in Section 5.5.1, below. Such compounds also may include other cellular proteins.

Compounds identified via assays such as those described herein may be useful, for example, in elaborating the biological function of the compounds, and for ameliorating melanomas disease. In instances whereby a melanoma results from an overall lower level of target gene expression and/or target gene product in a cell or tissue, compounds that interact with the target gene product may include compounds which accentuate or amplify the activity of the bound target gene protein. Such compounds would bring about an effective increase in the level of target gene product activity, thus ameliorating symptoms.

In some cases, a target gene observed to be up-regulated under disease conditions may be exerting a protective effect. Compounds that enhance the expression of such up-regulated genes, or the activity of their gene products, also would ameliorate disease symptoms, especially in individuals whose target gene is not normally up-regulated.

In other instances, mutations within the target gene may cause aberrant types or excessive amounts of target gene proteins to be made which have a deleterious effect that leads to melanomas. Similarly, physiological conditions may cause an excessive increase in target gene expression leading to melanomas. In such cases, compounds that bind target gene protein may be identified that inhibit the activity of the bound target gene protein.

5.6.1 In Vitro Screening Assays for Compounds that Bind to the Target Gene Product In vitro systems may be designed to identify compounds capable of binding to target genes of the invention. Such compounds may include, but are not limited to, peptides made of D- and/or L-configuration amino acids (m, for example, the form of random peptide libraries; see e.g., Lam, K. S. et al., 1991, Nature 354:82-84), phosphopeptides (m, for example, the form of random or partially degenerate, directed phosphopeptide libraries; see, e.g., Songyang, Z. et al., 1993, Cell 72:767-778), antibodies, and small organic or inorganic molecules. Compounds identified may be useful, for example, in modulating the activity of target gene proteins, preferably mutant target gene proteins, may be useful in elaborating the biological function of the target gene protein, may be utilized in screens for identifying compounds that disrupt normal target gene interactions, or may in themselves disrupt such interactions.

The principle of the assays used to identify compounds that bind to the target gene protein involves preparing a reaction mixture of the target gene protein and the test compound under conditions and for a time sufficient to allow the two components to interact and bind, thus forming a complex which can be removed and/or detected in the reaction mixture. These assays can be conducted in a variety of ways. For example, one method to conduct such an assay would involve anchoring the target gene or the test substance onto a solid phase and detecting target gene/test substance complexes anchored on the solid phase at the end of the reaction. In one embodiment of such a method, the target gene protein may be anchored onto a solid surface, and the test compound, which is not anchored, may be labeled, either directly or indirectly.

In practice, microtitre plates are conveniently utilized. The anchored component may be immobilized by non-covalent or covalent attachments. Non-covalent attachment may be accomplished simply by coating the solid surface with a solution of the protein and drying. Alternatively, an immobilized antibody, preferably a monoclonal antibody, specific for the protein may be used to anchor the protein to the solid surface. The surfaces may be prepared in advance and stored.

In order to conduct the assay, the nonimmobilized component is added to the coated surface containing the anchored component. After the reaction is complete, unreacted components are removed (e.g., by washing) under conditions such that any complexes formed will remain immobilized on the solid surface. The detection of complexes anchored on the solid surface can be accomplished in a number of ways. Where the previously nonimmobilized component is pre-labeled, the detection of label immobilized on the surface indicates that complexes were formed. Where the previously nonimmobilized component is not pre-labeled, an indirect label can be used to detect complexes anchored on the surface; e.g., using a labeled antibody specific for the previously nonimmobilized component (the antibody, in turn, may be directly labeled or indirectly labeled with a labeled anti-Ig antibody).

Alternatively, a reaction can be conducted in a liquid phase, the reaction products separated from unreacted components, and complexes detected; e.g., using an immobilized antibody specific for target gene product or the test compound to anchor any complexes formed in solution, and a labeled antibody specific for the other component of the possible complex to detect anchored complexes. Compounds that are shown to bind to a particular target gene product through one of the methods described above can be further tested for their ability to elicit a biochemical response from the target gene protein.

5.6.2 Assays for Compounds that Interfere With Interaction Between Target Gene Product and Other Compounds The target gene proteins of the invention may, in vivo, interact with one or more cellular or extracellular proteins. For the purposes of this discussion, target gene products and such cellular and extracellular proteins are referred to herein as "binding partners". Compounds that disrupt such interactions may be useful in regulating the activity of the target gene proteins, especially mutant target gene proteins. Such compounds may include, but are not limited to molecules such as antibodies, peptides, and the like described in Section 5.5.1. above.

The basic principle of the assay systems used to identify compounds that interfere with the interaction between the target gene protein, and its cellular or extracellular protein binding partner or partners involves preparing a reaction mixture containing the target gene protein and the binding partner under conditions and for a time sufficient to allow the two proteins to interact and bind, thus forming a complex. In order to test a compound for inhibitory activity, the reaction mixture is prepared in the presence and absence of the test compound. The test compound may be initially included in the reaction mixture or may be added at a time subsequent to the addition of target gene and its cellular or extracellular binding partner. Control reaction mixtures are incubated without the test compound or with a placebo. The formation of any complexes between the target gene protein and the cellular or extracellular binding partner is then detected. The formation of a complex in the control reaction, but not in the reaction mixture containing the test compound, indicates that the compound interferes with the interaction of the target gene protein and the interactive binding partner protein. Additionally, complex formation within reaction mixtures containing the test compound and a normal target gene protein may also be compared to complex formation within reaction mixtures containing the test compound and mutant target gene protein. This comparison may be important in those cases wherein it is desirable to identify compounds that disrupt interactions of mutant but not normal target gene proteins.

The assay for compounds that interfere with the interaction of the binding partners can be conducted in a heterogeneous or homogeneous format. Heterogeneous assays involve anchoring one of the binding partners onto a solid phase and detecting complexes anchored on the solid phase at the end of the reaction. In homogeneous assays, the entire reaction is carried out in a liquid phase. In either approach, the order of addition of reactants can be varied to obtain different information about the compounds being tested. For example, test compounds that interfere with the interaction between the binding partners, e.g., by competition, can be identified by conducting the reaction in the presence of the test substance; i.e., by adding the test substance to the reaction mixture prior to or simultaneously with the target gene protein and interactive cellular or extracellular protein. Alternatively, test compounds that disrupt preformed complexes, e.g. compounds with higher binding constants that displace one of the binding partners from the complex, can be tested by adding the test compound to the reaction mixture after complexes have been formed. The various formats are described briefly below.

In a heterogeneous assay system, either the target gene protein or the interactive cellular or extracellular binding partner protein, is anchored onto a solid surface, and its binding partner, which is not anchored, is labeled, either directly or indirectly. In practice, microtitre plates are conveniently utilized. The anchored species may be immobilized by non-covalent or covalent attachments. Non-covalent attachment may be accomplished simply by coating the solid surface with a solution of the protein and drying. Alternatively, an immobilized antibody specific for the protein may be used to anchor the protein to the solid surface. The surfaces may be prepared in advance and stored.

In order to conduct the assay, the binding partner of the immobilized species is exposed to the coated surface with or without the test compound. After the reaction is complete, unreacted components are removed (e.g., by washing) and any complexes formed will remain immobilized on the solid surface. The detection of complexes anchored on the solid surface can be accomplished in a number of ways. Where the binding partner was pre-labeled, the detection of label immobilized on the surface indicates that complexes were formed. Where the binding partner is not pre-labeled, an indirect label can be used to detect complexes anchored on the surface; e.g., using a labeled antibody specific for the binding partner (the antibody, in turn, may be directly labeled or indirectly labeled with a labeled anti-Ig antibody). Depending upon the order of addition of reaction components, test compounds which inhibit complex formation or which disrupt preformed complexes can be detected.

Alternatively, the reaction can be conducted in a liquid phase in the presence or absence of the test compound, the reaction products separated from unreacted components, and complexes detected; e.g., using an immobilized antibody specific for one binding partner to anchor any complexes formed in solution, and a labeled antibody specific for the other binding partner to detect anchored complexes. Again, depending upon the order of addition of reactants to the liquid phase, test compounds which inhibit complex or which disrupt preformed complexes can be identified.

In an alternate embodiment of the invention, a homogeneous assay can be used. In this approach, a preformed complex of the target gene protein and the interactive cellular or extracellular protein is prepared in which one of the binding partners is labeled, but the signal generated by the label is quenched due to complex formation (see, e.g., U.S. Pat. No. 4,109,496 by Rubenstein which utilizes this approach for immunoassays). The addition of a test substance that competes with and displaces one of the binding partners from the preformed complex will result in the generation of a signal above background. In this way, test substances which disrupt target gene protein-cellular or extracellular protein interaction can be identified.

In another embodiment of the invention, these same techniques can be employed using peptide fragments that correspond to the binding domains of the target gene protein and the interactive cellular or extracellular protein, respectively, in place of one or both of the full length proteins. Any number of methods routinely practiced in the art can be used to identify and isolate the protein's binding site. These methods include, but are not limited to, mutagenesis of one of the genes encoding the proteins and screening for disruption of binding in a co-immunoprecipitation assay. Compensating mutations in the target gene can be selected. Sequence analysis of the genes encoding the respective proteins will reveal the mutations that correspond to the region of the protein involved in interactive binding. Alternatively, one protein can be anchored to a solid surface using methods described in this Section above, and allowed to interact with and bind to its labeled binding partner, which has been treated with a proteolytic enzyme, such as trypsin. After washing, a short, labeled peptide comprising the binding domain may remain associated with the solid material, which can be isolated and identified by amino acid sequencing. Also, once the gene coding for the for the cellular or extracellular protein is obtained, short gene segments can be engineered to express peptide fragments of the protein, which can then be tested for binding activity and purified or synthesized.

A particular embodiment of the invention features a method of screening candidate compounds for their ability to antagonize the interaction between ligand and the receptor domain of a target gene product. The method involves: a) mixing a candidate antagonist compound with a first compound which includes a recombinant target gene product comprising a receptor domain (or ligand-binding fragment or analog) on the one hand and with a second compound which includes ligand on the other hand; b) determining whether the first and second compounds bind; and c) identifying antagonistic compounds as those which interfere with the binding of the first compound to the second compound.

By an "antagonist" is meant a molecule which inhibits a particular activity, in this case, the ability of ligand to interact with a target gene product receptor domain and/or to trigger the biological events resulting from such an interaction. Preferred therapeutics include antagonists, e.g., peptide fragments (particularly, fragments derived from the N-terminal extracellular domain), antibodies (particularly, antibodies which recognize and bind the N-terminal extracellular domain), or drugs, which block ligand or target gene product function by interfering with the ligand-receptor interaction.

Because the receptor component of the target gene product can be produced by recombinant techniques and because candidate antagonists may be screened in vitro, the instant invention provides a simple and rapid approach to the identification of useful therapeutics.

Specific receptor fragments of interest include any portions of the target gene products that are capable of interaction with ligand, for example, all or part of the N-terminal-extracellular domain. Such portions include the transmembrane segments and portions of the receptor deduced to be extracellular. Such fragments may be useful as antagonists (as described above), and are also useful as immunogens for producing antibodies which neutralize the activity of the target gene product in vivo (e.g., by interfering with the interaction between the receptor and ligand; see below). Extracellular regions may be identified by comparison with related proteins of similar structure, useful regions are those exhibiting homology to the extracellular domains of well-characterized members of the family.

Binding of ligand to its receptor may be assayed by any of the methods described above in Section 5.5.1. Preferably, cells expressing recombinant target gene product (or a suitable target gene product fragment or analog) are immobilized on a solid substrate (e.g., the wall of a microtitre plate or a column) and reacted with detectably-labeled ligand (as described above). Binding is assayed by the detection label in association with the receptor component (and, therefore, in association with the solid substrate). Binding of labeled ligand to receptor-bearing cells is used as a "control" against which antagonist assays are measured. The antagonist assays involve incubation of the target gene product-bearing cells with an appropriate amount of candidate antagonist. To this mix, an equivalent amount to labeled ligand is added.

Appropriate candidate antagonists include target gene product fragments, particularly fragments containing a ligand-binding portion adjacent to or including one or more transmembrane segments or an extracellular domain of the receptor (described above); such fragments would preferably including five or more amino acids. Other candidate antagonists include analogs of ligand and other peptides as well as non-peptide compounds and anti-target gene product antibodies designed or derived from analysis of the receptor.

6 EXAMPLE 1

Down-Regulation of E-Cadherin by ET-1

This example demonstrates the down-regulation of E-cadherin by ET-1.

6.1 Materials and Methods

A375, WM-266-4 and WM-1 15 melanoma cells were purchased from the ATCC. Culture conditions were as described in I. M. Shih, et al., *Am. J. Pathol.*, 145:837-45 (1994). Two weeks prior to ET-stimulation, water soluble 12,13-phorbol dibutyrate was substituted for phorbol 12-myristate, 13-acetate in melanocyte medium. ET stimulations of melanocytes were carried out in phorbol-free medium. Cell pellets were incubated for 15 minutes in 6 pellet volumes of RIPA buffer (1% NP4O, 0.5% deoxycholic acid, 10 mM Tris pH 8.3, 150 mM NaCl, 50 mM NaF, 0.2 mM sodium vanadate, 1× protease inhibitors-Boehringer complete). After centrifugation, lysates were quantitated using protein assay reagent (Biorad). 2.5 ug of protein per sample were subjected to SDS-PAGE unless samples were prepared from A375, WM-266-4 or WM-1 15 cells in which case 100 ug protein per sample was used. BQ123 and BQ788 at 100 nM were added to cells one hour before ET-1 addition. Antibodies: anti-E-cadherin (Transduction labs), anti-mouse IgG-HRP (Santa-Cruz). ECL detection system (Amersham). ET-1, ET-3, BQ123, BQ788 (Peninsula labs).

6.2 Results

Human neonatal melanocytes (FM2030) and human melanoma cells (SKMEL28) were stimulated with 10 nM ET-1 over a 40 hour time-course and protein lysates were examined for E-cadherin protein levels by immunoblot analysis (FIG. 1A). By 40 hours, a marked decrease in E-cadherin protein was evident. E-cadherin protein levels returned to baseline by 72 hours. A delayed and prolonged response to ET-1 has also been reported in other cell types. R. Marsault, et al., *Biochem. Biophys. Res. Commun.,* 179:1408-13 (1991). One additional melanocyte cell line (CL-NHEM) and 4 additional melanoma cell lines were stimulated with ET-1, and down-regulation of E-cadherin was observed in all lines except in A375 and WM-115 melanoma cells in which E-cadherin protein was undetectable at baseline (FIG. 1B). In addition to E-cadherin, expression of the adhesion molecules ICAM-1, CD44 and N-cadherin is altered during melanoma development. M. Y. Hsu, et al., *J. Investig. Dermatol. Symp. Proc.,* 1:188-94 (1996); S. Vermeulen, et al., *Pathol. Res. Pract.,* 192:694-707 (1996). However, immunoblot analysis of lysates revealed no effect of ET-1 upon protein levels of these adhesion molecules, thus the effect of ET-1 was specific for E-cadherin. Northern blot analysis was performed and no ET-1-dependent decrease in E-cadherin mRNA levels was detected suggesting a post-transcriptional mechanism of down-regulation.

There are two well characterized ET-1 receptors, an A subtype (ETA) and a B subtype (ETB). A. G. Baynash, et al., *Cell,* 79:1277-85 (1994). Both subtypes are expressed by melanocytes while most melanoma cells express only ETB. ET-1 binds with equal affinity to both receptor subtypes. G. Imokawa, et al., *Biochem. J,* 314:305-12 (1996). To determine which subtype mediated the observed response, the assay was repeated in the presence of a selective ETA antagonist (BQ123) and a selective ETB antagonist (BQ788). BQ788, but not BQ123, blocked E-cadherin down-regulation by ET-1 suggesting that ETB activation is required for this response to occur (FIG. 1C). Down-regulation of E-cadherin by ET-1 is dose-responsive in both melanocytes and melanoma cells (FIG. 1D). ET-3, a selective ETB agonist, is also a potent down-regulator of E-cadherin (FIG. 1D, last lane) supporting the results that ETB mediates the response.

7 EXAMPLE 2

Down-Regulation of β-Catenin and p120$^{CTN}$ by ET-1

This example the down-regulation of β-Catenin and p120$^{CTN}$ by ET-1.

7.1 Materials and Methods

To analyze membrane-associated catenin proteins, crude membrane fractions were prepared as follows: cell pellets were resuspended in 6 pellet volumes of buffer A (10 mM HEPES pH 7.5, 1.5 mM MgCl$_2$, 10 mM KCl, 10 mM NaF, 0.2 mM sodium vanadate, 1× protease inhibitors—Boehringer complete) and allowed to swell for 10 min. Cell membranes were disrupted by vortexing for 10s and membranes pelleted by centrifugation for 10s. Supernatants containing cytoplasmic proteins were discarded. Membrane pellets were solubilized in RIPA buffer as described above and snap frozen on dry ice. 0.5 ug and 2.5 ug of protein lystes were used to examine levels of β-catenin and p120$^{CTN}$ proteins respectively. Antibodies: anti-β-catenin and anti-p120$^{CTN}$ (Transduction labs).

7.2 Results

The catenins are cytoplasmic proteins that bind E-cadherin and are critical for E-cadherin function in cellular adhesion. J. M. Daniel, et al., *Bloessays,* 19: 883-91 (1997). Considering the importance of the catenins in E-cadherin function, the effect of ET-1 stimulation upon the levels of these proteins was studied. In both melanocytes and melanoma cells, ET-1 stimulation decreased β-catenin protein levels and increased its electrophoretic mobility (FIG. 2A). The kinetics of this response correlated well with those of E-cadherin down-regulation. BQ788, a selective ETB antagonist, blocked ET-1 mediated down-regulation of β-catenin (FIG. 2B). As with E-cadherin, northern blot analysis failed to reveal an ET-1- dependent decrease in β-catenin mRNA levels, suggesting a post-transcriptional mechanism of down-regulation. ET-1 also down-regulated and increased the electrophoretic mobility of p120$^{CTN}$, another catenin family member, with kinetics paralleling those observed for E-cadherin and β-catenin down-regulation (FIG. 2C). These results suggest that ET-1 down-regulates E-cadherin by post-translational modification of catenin proteins which likely renders them unable to form stable complexes with E-cadherin at the plasma membrane.

8 EXAMPLE 3

Caspase-8 Activation by ET-1

8.1 Materials and Methods

All caspase inhibitors contained a 16 amino-acid signal peptide derived from Kaposi Fibroblast Growth Factor to confer cell permeability (Calbiochem). Inhibitors were added to cells 34 hours post ET-1 stimulation and cells harvested at 40 hours. Crude cytoplasmic fractions were prepared as described for FIG. 2, except that supernatants containing cytoplasmic proteins were transferred to new tubes, supplemented with 0.11 volumes of buffer B (0.3M HEPES pH 7.9, 1.4M KCl, 0.03M MgCl$_2$) and clarified by centrifugation. 10 ug of protein per sample was analyzed for caspase activation. Antibodies: Anti-caspase-8 antibody (UBI), Anti-caspase-3 and 7 (Transduction labs). Super Signal West Femto Maximum Sensitivity Substrate (PIERCE) was used for chemiluminescent detection of caspase proteins. Membranes were initially developed in a 1:5 dilution of the reagent made in H$_2$O. If necessary, blots were briefly rinsed in TBS (10 mM Tris pH 8.0, 150 mM NaCl) and redeveloped with undiluted reagent for visualization of small fragments.

8.2 Results

Caspases are proteases best known for their role in apoptotic cell death but also participate in inflammatory processes. N. A. Thomberry, et al, *Science,* 261:1312-8 (1998). Several studies have shown that proteases belonging to the caspase family cleave β-catenin during apoptosis with a concomitant down-regulation of E-cadherin. B. Herren, et al., *Mol. Biol. Cell.,* 9:1589-601 (1998). Caspase-3 cleavage of β-catenin at a C-terminal site generates a 90 kD fragment from the 92 kD protein. This 90 kD fragment demonstrates a slight increase in electrophoretic mobility over the 92 kD fragment. In addition, the ability of ET-1 to induce apoptosis in a small percentage of cells derived from melanoma cell line A375, suggests that ET-1 is capable of activating caspase family members. M. Okazawa, et al, *J. Biol. Chem.,* 273:12584-92 (1998).

To determine whether caspase activation played a role in down-regulation of E-cadherin by ET-1, the assay was repeated in the presence of cell-permeable inhibitors of a variety of different caspases (FIG. 3A). Strikingly, inhibitors containing the sequences IETD (inhibition of caspase-8) and DEVD (inhibition of caspases-3,7,8) were able to block down-regulation of E-cadherin by ET-1. The 'DEVD' inhibitor required a 10-fold higher concentration than the 'IETD' inhibitor in order to be effective (FIG. 3A, lower panel). Inhibitors specific for caspases 1, 4, 5, 6, 9 and 10 were without effect. Inhibition of caspase-8 also blocked down-regulation of β-catenin and p120$^{CTN}$ (FIG. 3B). These results suggested that caspases 3, 7 and/or 8 are activated in response to ET-1 stimulation and participate in down-regulation of E-cadherin, β-catenin and p120$^{CTN}$. Immunoblot analysis revealed that of these caspases, only caspase-8 underwent ET-1-dependent proteolytic processing which was first detectable approximately 36 hours after ET-1 stimulation and lasted for 4-6 hours (FIG. 3C, upper panel). Timepoints of maximal E-cadherin down-regulation coincided with the appearance of catalytically active caspase-8 subfragments (FIG. 3C, lower panel). Treatment of cells with a cell permeable inhibitor of caspase-8 prevented its proteolytic processing providing further evidence that caspase-8 activation is required for down-regulation of E-cadherin, β-catenin and p120$^{CTN}$ by ET-1.

Caspases are activated in a sequential cascade beginning with apical caspases such as caspase-8 which then activate distal caspases such as caspases-3 and 7 which execute apoptotic cell death through cleavage of a variety of critical cell substrates. N. A. Thomberry, et al, *Science,* 261; 1312-8 (1998). The apparent failure of ET-1 to activate distal caspases despite the activation of caspase-8 (FIG. 3D) is consistent with the failure to induce apoptosis in the cells. Cleavage of immunoprecipitated β-catenin and p120$^{CTN}$ by recombinant caspase-8 in vitro also was not demonstrated, thus its effect upon catenin proteins may be indirect.

8.3 Discussion

Overall, the results demonstrate that ET-1 down-regulates E-cadherin through a mechanism requiring caspase-8 activation. Caspase-8 may directly cleave catenin proteins or activate other as of yet unidentified caspase(s) which cleave catenin proteins, and this cleavage likely leads to destabilization and disruption of E-cadherin:catenin complexes at the plasma membrane. Indeed, caspase cleavage has been shown to prevent interaction of β-catenin with α-catenin, the latter of which serves to anchor the E-cadherin:catenin complex to the actin cytoskeleton. B. Herren, et al., *Mol. Biol. Cell.,* 9: 1589-601 (1998).

9 EXAMPLE 4

Alteraton of Subcellular Localization of E-Cadherin and β-Catenin by ET-1

9.1 Materials and Methods

Cells were seeded onto collagen coated glass chamber slides in medium supplemented with 10 nM ET-1. At 48 hours, medium was aspirated and replaced with fresh ET-1 supplemented medium. At 96 hours, cells were fixed for 10 minutes in 3.7% formaldehyde/1 mM CaCl$_2$/PBS, permeabilized for 10 minutes in 0.2% Triton X-100/PBS and blocked in 1% BSA/PBS for 10 minutes. Staining with E-cadherin and β-catenin antibodies diluted 1:50 in blocking buffer was performed for 45 minutes followed by a 30 minute incubation with goat-anti-mouse IgG-Cy3 (Jackson Immunoresearch labs) diluted 1:200 in blocking buffer. Cells were washed with PBS in between permeabilization and fixation steps and after antibody incubations.

9.2 Results

Figures 4A, 4B:
Figures 4C, 4D:
Figures 4E, 4F:
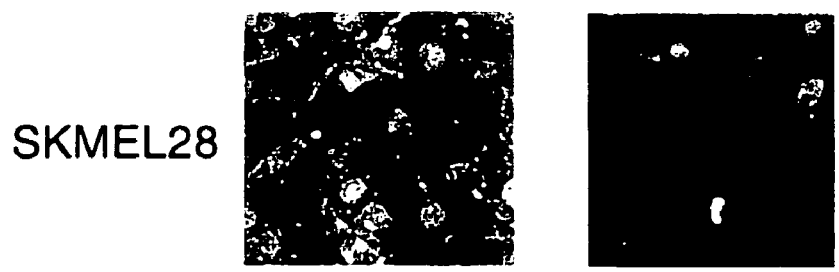

To investigate the effect of ET-1 on the subcellular localization of E-cadherin and β-catenin proteins, immunofluorescence studies were performed. When compared to unstimulated controls, ET-1-stimulated melanoma cells displayed a markedly decreased intensity of membranous staining using anti-E-cadherin antibody (FIGS. 4a, b). ET-1 stimulation of melanocytes resulted in loss of concentration of E-cadherin staining at points of cell:cell contact and the appearance of a punctate perinuclear staining pattern reminiscent of that seen in melanoma cells (FIGS. 4c, d). This punctate pattern appears to represent intracellular aggregates of dysfunctional E-cadherin. While unstimulated melanoma cells displayed both a membranous and nuclear staining-pattern using anti-β-catenin antibodies, ET-1 stimulation resulted in loss of most of the membranous staining while retaining a similar intensity of staining of the nucleus (FIGS. 4e, f). This demonstrates that ET-1 specifically targets the membrane-associated pool of β-catenin for down-regulation in these cells. ET-1 stimulation of melanocytes resulted in a loss of concentration of β-catenin at lateral cell borders and at points of cell:cell contact (FIGS. 4g, h). The resulting diffuse membranous staining pattern accentuates the morphological alteration induced by ET-1 stimulation which is shown more clearly in the bright-field micrographs (FIGS. 4i, j). Unstimulated melanocytes are bipolar with small nuclei, scant cytoplasm and participate in precise cell:cell contacts. In sharp contrast, ET-1 stimulated melanocytes have large nuclei with prominent nucleoli, abundant cytoplasm, polygonal morphology and grow in a haphazard fashion displaying loss of contact inhibition. These changes are consistent with cytoskeletal reorganization and down-regulation of E-cadherin at the plasma membrane.

Although the invention is described in detail with reference to specific embodiments thereof, it will be understood that variations which are functionally equivalent are within the scope of this invention. Indeed, various modifications of the invention in addition to those shown and described herein will become apparent to those skilled in the art from the foregoing description and accompanying drawings. Such modifications are intended to fall within the scope of the appended claims.

Various publications are cited herein, each of the disclosures of which is incorporated by reference in its entirety.

What is claimed is:

1. A method for treating metastatic melanoma in a patient in need thereof, comprising administering a therapeutically effective amount of a selective endothelin B receptor (ETB) antagonist to said patient, with the proviso that said method does not include gene therapy.

2. The method of claim 1, wherein the selective endothelin B receptor (ETB) antagonist is a peptide inhibitor.

3. The method of claim 1, wherein the selective endothelin B receptor (ETB) antagonist is an endothelin B receptor (ETB) antibody.

4. The method of claim 1, wherein the selective endothelin B receptor (ETB) antagonist is BQ788.

5. The method of claim 1, wherein the selective endothelin B receptor (ETB) antagonist is IRL-1038.

6. The method of claim 1, wherein the selective endothelin B receptor (ETB) antagonist is RES-701-1.

7. The method of claim 1, wherein said patient displays one or more atypical moles.

8. The method of claim 1, wherein the ability of the selective endothelin B receptor (ETB) antagonist to antagonize the endothelin B receptor (ETB) is determined in vitro by:
   a) contacting a cell culture expressing endothelin B receptor (ETB) and E-cadherin with endothelin and the compound;
   b) determining the level of E-cadherin expression; and
   c) comparing the level of E-cadherin expression determined in step b) to that of a control culture in the absence of said compound, so that an increase in expression of E-cadherin indicates antagonist activity.

9. A method for inhibiting the development of metastatic melanoma in a patient having melanoma, comprising administering a therapeutically effective amount of a selective endothelin B receptor (ETB) antagonist to said patient, with the proviso that said method does not include gene therapy.

10. The method of claim 9, wherein the selective endothelin B receptor (ETB) antagonist is a peptide inhibitor.

11. The method of claim 9, wherein the selective endothelin B receptor (ETB) antagonist is an endothelin B receptor (ETB) antibody.

12. The method of claim 9, wherein the selective endothelin B receptor (ETB) antagonist is BQ788.

13. The method of claim 9, wherein the selective endothelin B receptor (ETB) antagonist is IRL-1038.

14. The method of claim 9, wherein the selective endothelin B receptor (ETB) antagonist is RES-701-1.

15. The method of claim 9, wherein said patient displays one or more atypical moles.

16. The method of claim 9, wherein the ability of the selective endothelin B receptor (ETB) antagonist to antagonize the endothelin B receptor (ETB) is determined in vitro by:
   a) contacting a cell culture expressing endothelin B receptor (ETB) and E-cadherin with endothelin and the compound;
   b) determining the level of E-cadherin expression; and
   c) comparing the level of E-cadherin expression determined in step b) to that of a control culture in the absence of said compound, so that an increase in expression of E-cadherin indicates antagonist activity.

* * * * *